United States Patent [19]

Colligan et al.

[11] Patent Number: 5,394,971
[45] Date of Patent: Mar. 7, 1995

[54] APPARATUS FOR ATTACHING SURGICAL SUTURE COMPONENTS

[75] Inventors: Francis D. Colligan, Waterbury; Donald C. Ross, Orange, both of Conn.

[73] Assignee: United States Surgical Corporation, Norwalk, Conn.

[21] Appl. No.: 100,716

[22] Filed: Aug. 2, 1993

[51] Int. Cl.[6] .............................................. B65G 47/24
[52] U.S. Cl. .................................... 198/391; 198/396; 198/345.1; 198/468.6
[58] Field of Search ............ 198/389, 391, 396, 345.1, 198/468.11, 468.6, 747

[56] References Cited

U.S. PATENT DOCUMENTS

| | | |
|---|---|---|
| Re. 27,735 | 8/1973 | Shave et al. |
| Re. 31,084 | 11/1982 | Birks |
| 1,558,037 | 10/1925 | Morton |
| 1,578,543 | 3/1926 | Montgomery |
| 2,000,680 | 5/1935 | Weatherhead, Jr. |
| 2,067,568 | 1/1937 | Grünthal |
| 2,205,893 | 6/1940 | Unger |
| 2,411,079 | 11/1946 | Baule |
| 2,620,028 | 12/1952 | Kohut |
| 2,798,585 | 7/1953 | Bailey et al. ............ 198/391 |
| 2,813,442 | 11/1957 | Wingate |
| 2,958,929 | 11/1960 | Vineberg et al. |
| 2,983,898 | 5/1961 | Kalmar et al. |
| 3,055,412 | 9/1962 | Dibner |
| 3,130,489 | 4/1964 | Schlage |
| 3,251,216 | 5/1966 | Broske |
| 3,251,451 | 5/1966 | Latawiec ............ 198/391 |
| 3,253,328 | 5/1966 | Baldwin |
| 3,365,927 | 1/1968 | Lynch |
| 3,643,327 | 2/1972 | Jackson |
| 3,655,028 | 4/1972 | Hodgins ............ 198/391 |
| 3,710,924 | 1/1973 | Schultz ............ 198/391 |
| 3,771,343 | 11/1973 | Dawson |
| 3,774,806 | 11/1973 | Swart et al. ............ 198/389 X |
| 3,890,975 | 6/1975 | McGregor |
| 3,910,282 | 10/1975 | Messer et al. |
| 3,963,031 | 6/1976 | Hunter |
| 3,966,040 | 6/1976 | Hazelwood ............ 198/391 |
| 3,972,219 | 8/1976 | Riehl |
| 3,980,177 | 9/1976 | McGregor |
| 4,054,144 | 10/1977 | Hoffman et al. |
| 4,060,885 | 12/1977 | Hoffman et al. |
| 4,067,224 | 1/1978 | Birks |
| 4,072,041 | 2/1978 | Hoffman et al. |
| 4,192,171 | 3/1980 | Hamilton |
| 4,292,833 | 10/1981 | Lapp |
| 4,306,443 | 12/1981 | Matsutani |
| 4,361,948 | 12/1982 | Omata |
| 4,369,570 | 1/1983 | Madden et al. ............ 198/468.11 X |
| 4,498,222 | 2/1985 | Ono et al. |
| 4,567,650 | 2/1986 | Balyasny et al. |
| 4,719,789 | 1/1988 | Wiebe et al. |
| 4,722,384 | 2/1988 | Matsutani |
| 4,739,873 | 4/1988 | Yajima ............ 198/391 |
| 4,744,455 | 5/1988 | Dragotta et al. ............ 198/389 |
| 4,799,311 | 1/1989 | Matsutani |
| 4,836,006 | 6/1989 | Brown |
| 4,922,904 | 5/1990 | Uetake et al. |
| 5,038,461 | 8/1991 | Cerda |
| 5,046,350 | 9/1991 | Proto et al. |
| 5,099,676 | 3/1992 | Proto et al. |
| 5,115,904 | 5/1992 | Folk et al. |
| 5,131,131 | 7/1992 | Proto et al. |
| 5,168,619 | 12/1992 | Proto et al. |
| 5,230,352 | 7/1993 | Putnam et al. |
| 5,267,639 | 12/1993 | Amoh ............ 198/391 |

FOREIGN PATENT DOCUMENTS

| | | |
|---|---|---|
| 0249504 | 12/1987 | European Pat. Off. |
| 8715099 | 3/1988 | Germany |
| 3805772 | 9/1988 | Germany |
| 63-212027 | 9/1988 | Japan |
| 0296776 | 12/1988 | Japan |
| 1526222 | 9/1978 | United Kingdom |
| 1371856 | 2/1988 | U.S.S.R. ............ 198/391 |
| WO82/03579 | 10/1982 | WIPO |

*Primary Examiner*—D. Glenn Dayoan

[57] ABSTRACT

The present invention relates to an apparatus for attaching surgical sutures to eyeless surgical needles. The apparatus includes a system for automatically presenting the surgical needles to a frame which positions and maintains the needle for subsequent swaging and a rotating die system which selectively impacts the needle to secure the suture thereto.

14 Claims, 31 Drawing Sheets

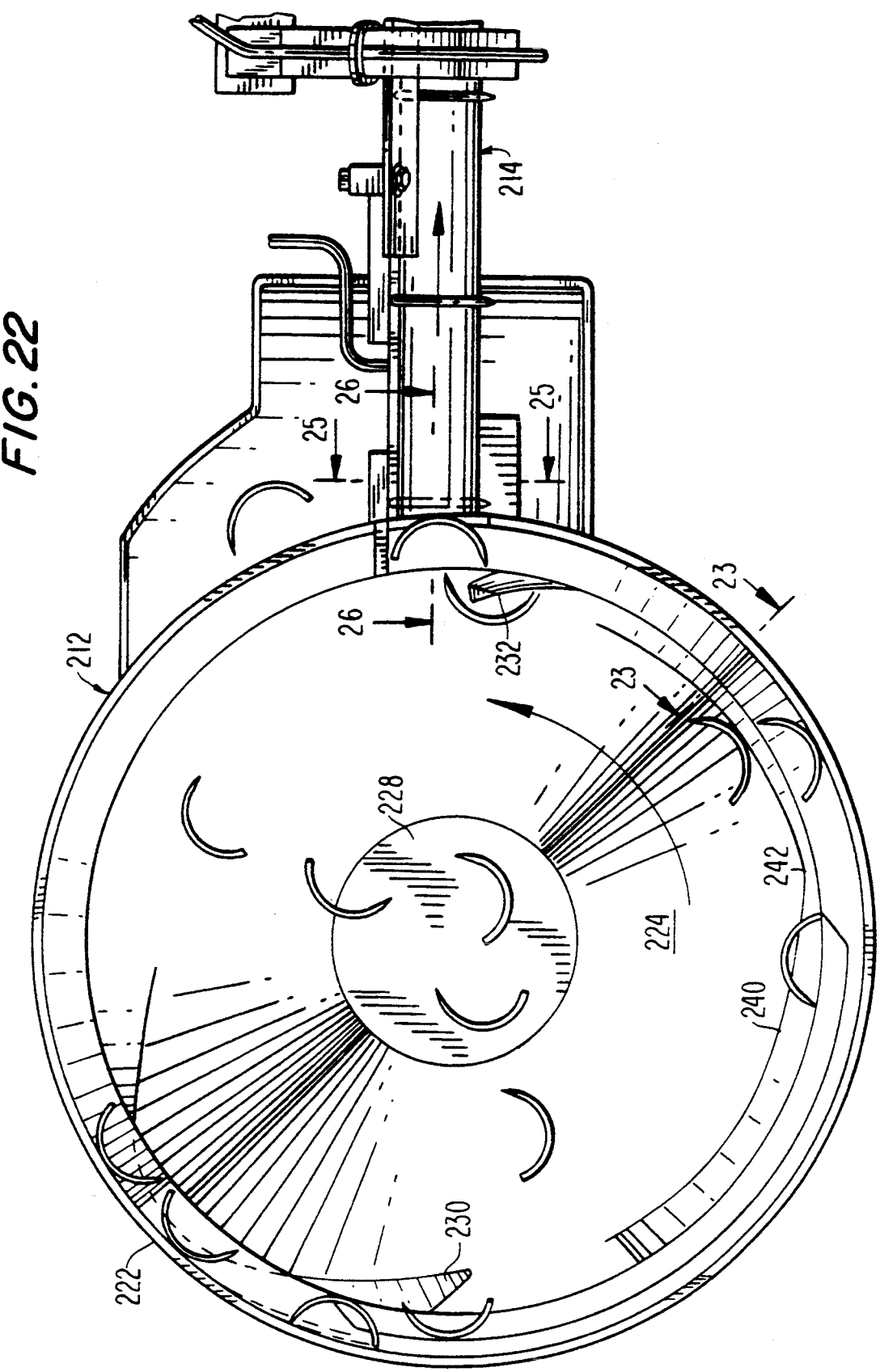

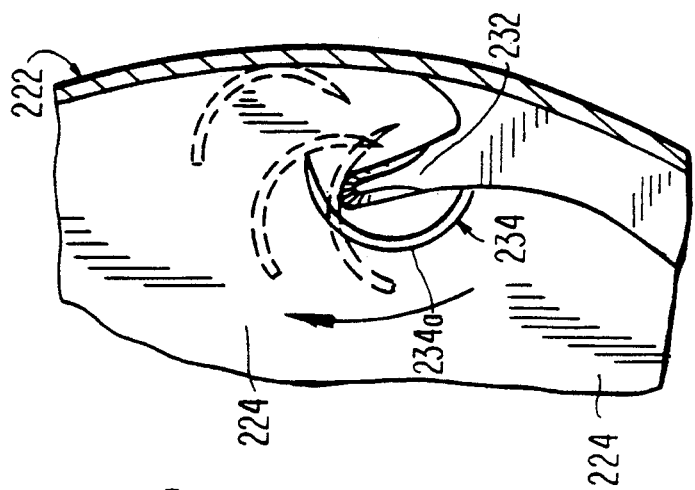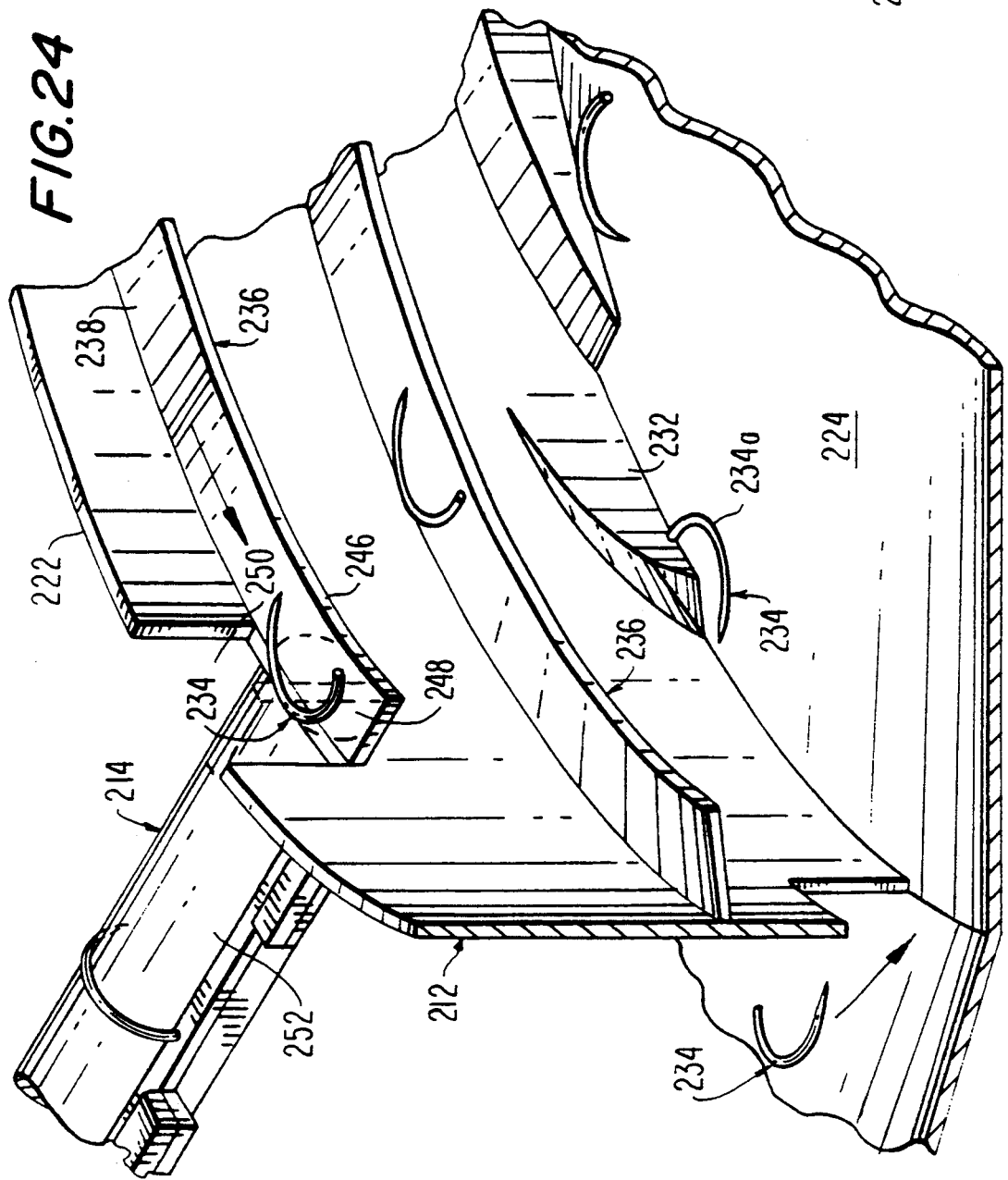

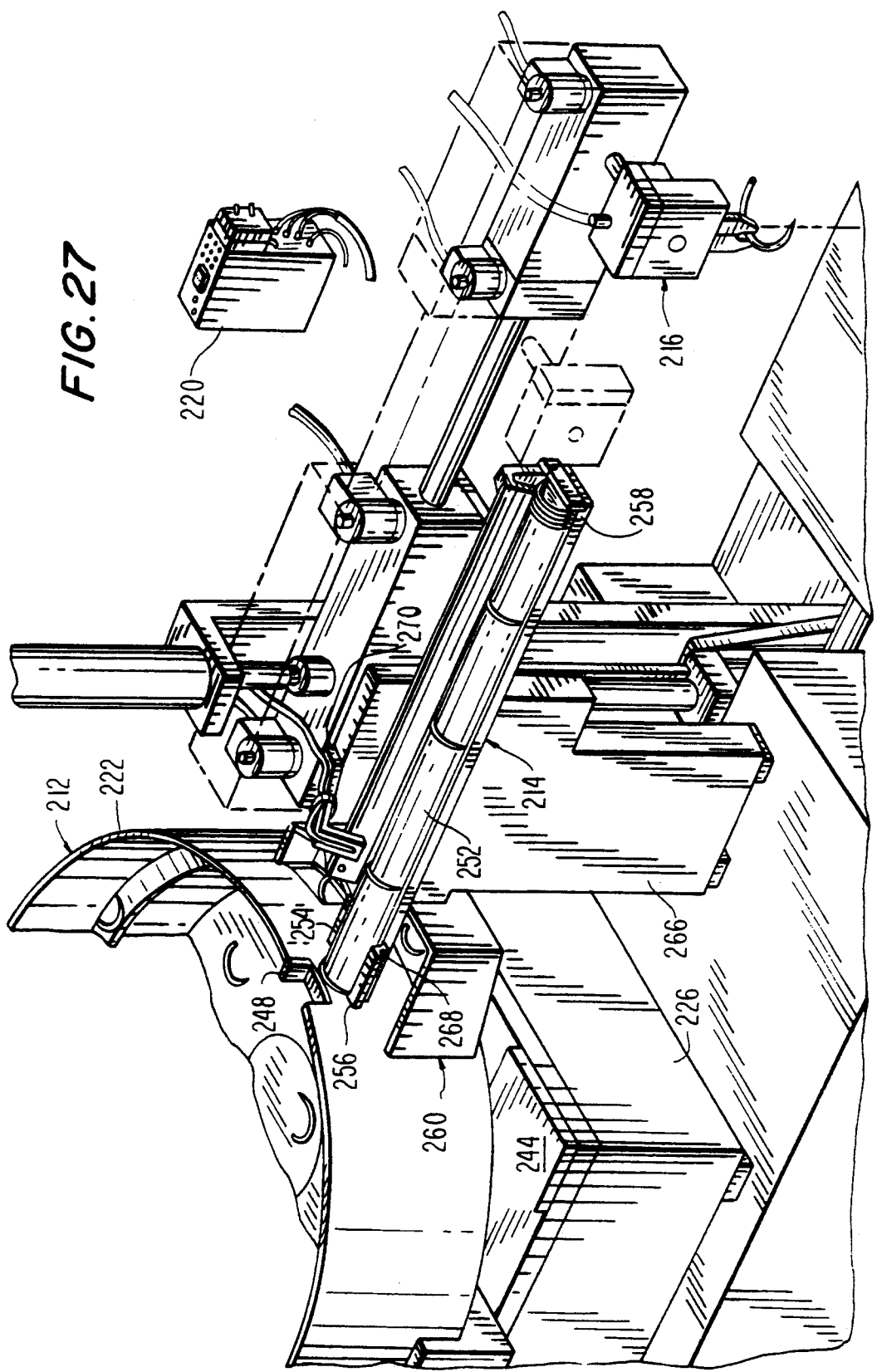

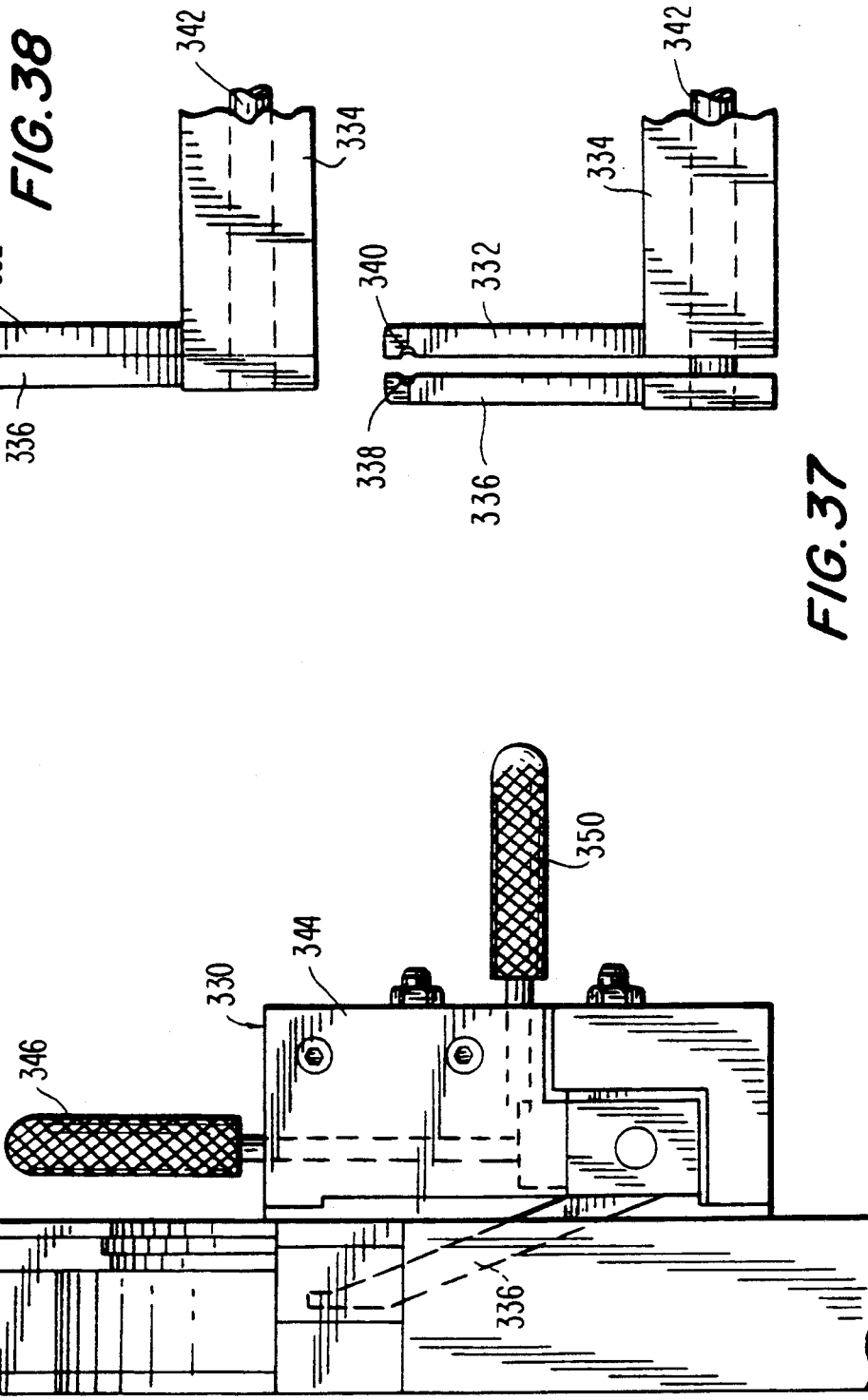

APPARATUS FOR ATTACHING SURGICAL SUTURE COMPONENTS

BACKGROUND OF THE INVENTION

1. Field of the Invention

The present invention relates to surgical sutures and their production. More particularly, the invention relates to an apparatus and method for attaching surgical needles to surgical sutures.

2. Description of the Related Art

The trend to develop and produce surgical sutures attached to eyeless surgical needles is continuously evolving. The most common surgical suture of this type is a single-use needle of appropriate size and shape which is attached to the end of the suture, so that the needle is used once and then discarded.

The attachment can be accomplished by use of a "drilled end" needle, that is, one in which a concentric aperture is formed in the end face of the needle, in which the suture is placed in the aperture and the needle is crimped around the suture. Alternatively, a "flanged" needle may be utilized in which a U-shaped channel is stamped into the end of the needle with the ends of the "U" being crimped about the suture to hold the suture together. The attachment must be one which is predictably secure, causes a minimum of damage to tissue, is convenient for the using surgeon, permits sterilization and entails reasonable costs. In addition, the attachment must withstand the rigors of manufacture, sterilization, storage, shipment and use.

With conventional crimping operations a crimp is created between several dies which close to a fixed gap. Any variation in the crimping dies, the needle size, the hole size, or the suture size alters the degree of crimp.

Conventional crimping methods require the back end of the needle be struck with two half moon shaped dies. The needle is then manually rotated 90° and the needle is struck again with the dies. The manual intervention in the production of surgical sutures with eyeless needles reduces production efficiency and increases the associated costs incurred in their manufacture. Manual intervention also adds to the operator's fatigue caused by continuous repetitive movement as well as the non-ergonomic design of such crimping apparatus.

To date, techniques devised for connecting such suture components in a manner to perform within the preferred guidelines are not as effective for high speed production of surgical sutures as would otherwise be desirable.

SUMMARY OF THE INVENTION

The present invention relates to an apparatus for feeding surgical needles to a needle crimping apparatus while minimizing occurrences of needle point damage. The needle crimping apparatus avoids the aforementioned disadvantages of conventional crimping operations by automatically rotating a pair of dies approximately 90° so as to reduce the need for manual rotation of the needle as described above. The needle feeding apparatus includes a container adapted to receive curved surgical needles and orientating the surgical needles in a predefined position for subsequent processing, a transmission member for receiving the orientated needles from the container at a receiving position and transferring the needles to a presenting position, and means for transferring the needles between the presenting position and a crimping position.

Preferably, the container is an uncoated vibratory bowl which has at least one sweep positioned on a bottom portion of the bowl and at least one ramp which orientates the needles while transferring the needles from the bottom portion of the bowl to the receiving position and substantially avoiding needle point damage.

The transmission member of the present invention includes a vibratory rail with a substantially cylindrical shape which is adapted to support and transfer the needles to the presenting position. Preferably, the rail has a radius equal to or less than the radius of curvature of the curved surgical needle so as to prevent damage to the needle point.

The transferring means of the present invention includes means for grasping needles in the presenting position and for transferring the grasped needle to a needle pusher track, and means for moving the needle along the pusher track to the crimping position. The grasping and transferring means has a drive member adapted for movement between the presenting position and the crimping position, and a pair of jaws secured to the drive member and movable between an open position and a closed position.

In an alternative embodiment a system for attaching surgical sutures to surgical needles is provided. Generally, the system utilizes the above described needle feeding apparatus to feed the surgical needles to a suture attaching apparatus. The system includes means for receiving and orienting surgical needles in a predefined arrangement, means for receiving the oriented needles from the receiving and orienting means and for transferring the needles to a presenting position, means for transferring the needles between the presenting position and a crimping position, and means for crimping a surgical suture to the transferred needles.

The system also includes means for guiding the surgical suture into a bore in the end face of the needle. The suture guide means has a first guide arm and a second guide arm arranged so that at least one of the first and second guide arms is movable either automatically or manually relative to the other. The first and second guide arms are adapted to receive a suture and direct the suture into the bore in the end face of the needle.

The crimping means of the above described system includes support means, die means attached to the support means for selectively impacting the needle so that a portion of the needle is deformed to maintain the suture therein, the die means being rotatable between at least two positions. First drive means is provided for actuating the die means to impact the needle, and second drive means is provided for rotating the die means at least to a second position respective to the needle.

Generally, the die means includes a die cartridge having at least one jaw slidably secured thereto and gear means secured to the die cartridge and operatively connected to the second drive means for translating movement of the second drive means to rotational movement of the die cartridge.

The first drive means includes a first pair of arms pivotally connected to a first drive member and positioned adjacent the die cartridge on opposite sides thereof and a second pair of arms pivotally connected to the first drive member and positioned adjacent the die cartridge on opposite sides thereof and out of phase with the first pair of arms.

The second drive means is adapted to rotate the die means between the first and second positions. In the preferred embodiment, the die means is adapted to impact the needle in the first and second positions, where the second position is rotatably oriented at least a predetermined angular position from the first position. Preferably, the second position is oriented at least about 90° from the first position. The second drive means includes rack gear means secured to a second drive member and adapted for engagement with the gear means such that linear movement of the rack gear means causes rotational movement of the die cartridge.

The apparatus also includes needle gripping means for maintaining the needle in a predetermined position when the die means is actuated. In addition, the apparatus of the present invention may further include guide means positioned adjacent the die means for guiding the suture into a bore in the end face of the needle. The guide means is adjustable in at least two directions, preferably, horizontal and vertical.

Control means is provided and operatively connected to the first and second drive means for selectively activating the first and second drive means. Generally, the control means includes pneumatic and electrical controls and switch means for automatically terminating the impacting and the rotation of the die means.

The present invention also provides a vibrating container for receiving and orientating curved surgical needles. The container includes a base, at least one side wall, and a needle receiving member positioned on the base. Sweeps are positioned on the base and are provided for orienting the curved surgical needles to a predetermined orientation. A ramp is secured to the side wall of the container and is provided to process the curved surgical needles from the base to a needle presenting position on the side wall. Preferably, the container is a stainless-steel bowl.

The present invention also provides a method for attaching surgical suture components. The method includes the following steps automatically feeding a surgical needle having a bore in an end face, from a needle container to a position between a pair of dies, releasably maintaining the needle between the pair of dies, inserting a surgical suture into the needle bore, and impacting the needle with the pair of dies so as to secure the suture to the needle.

In an alternative embodiment, after the needles are initially impacted, the dies may be rotated, preferably 90 degrees, and the needle is then impacted a second time to further secure the suture to the needle.

BRIEF DESCRIPTION OF THE DRAWINGS

Preferred embodiments of the invention are described hereinbelow with reference to the drawings wherein:

FIG. 22 is a top plan view of the needle bowl of FIG. 21, illustrating sweeps and a narrowed ramp portion for orienting needles for subsequent presentation to the rail feeding system;

FIG. 23 is a top plan view of a portion of the needle bowl of FIG. 22, illustrating the orientation of a needle by a sweep positioned on the base of the bowl;

FIG. 24 is a partial cross-sectional view of the needle bowl of FIG. 22, illustrating a needle properly positioned for presentation to the rail feeding system and a sweep in the lower portion of the bowl for properly orienting the needle with its barrel portion facing the center of the bowl;

FIG. 27 is a perspective view of the rail feeding system and the pick and place system of the present invention;

FIG. 37 is a side elevational view, greatly enlarged, of the jaws of the needle suture guide FIG. 36, illustrating the jaws in an open position;

FIG. 38 is a side elevational view of the jaws of the needle suture guide similar to FIG. 37, illustrating the jaws in a closed position;

FIG. 40 is a front plan view of the automatically operated needle suture guide of FIG. 36, illustrating two of the three dimensional adjusting screws.

DETAILED DESCRIPTION OF THE PREFERRED EMBODIMENTS

Figure 1:
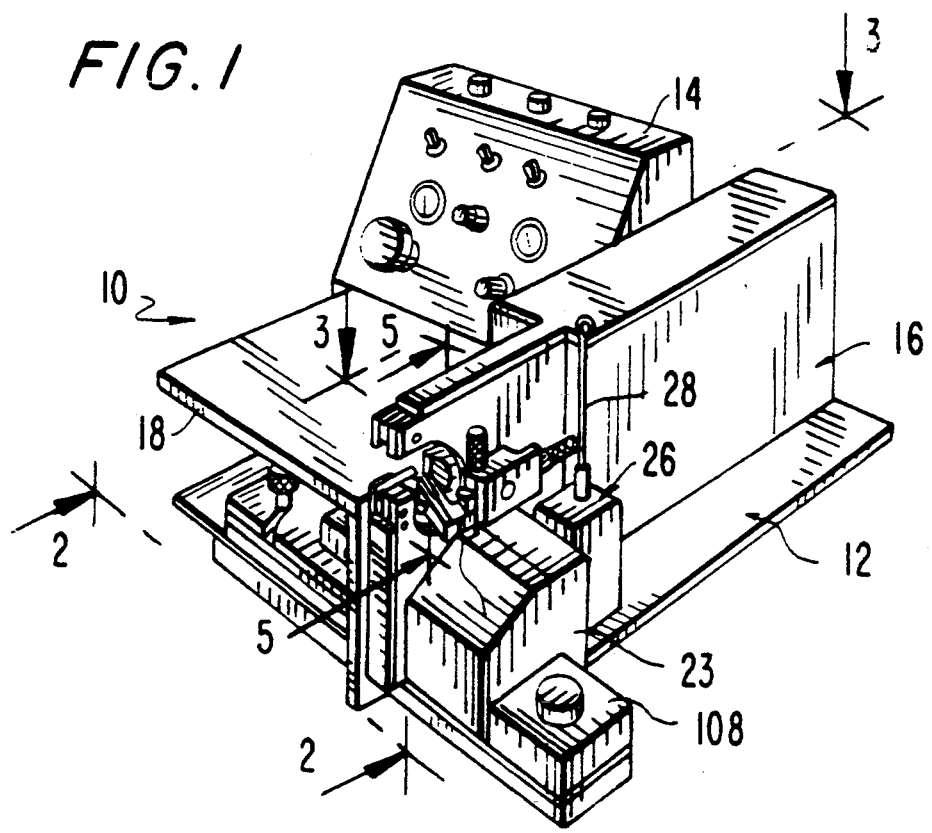
FIG. 1 is a perspective view of the suture needle attaching apparatus of the present invention.

Referring initially to FIG. 1, the apparatus 10 generally includes frame 12 to support the various components of the apparatus, control panel 14 and die rotating and crimping system 16. Control panel 14 may be secured to, or independent of frame 12 and provides electrical and pneumatic controls for the active components of apparatus 10. The electrical and pneumatic controls and devices for control panel 14 are preferably of a type known in the art and include, for example, electrical and pneumatic switches, air pressure gauges and light indicators. Die rotating and crimping system 16 is secured to frame 12 as shown and is provided to rotate and crimp the crimping dies.

Figure 2:
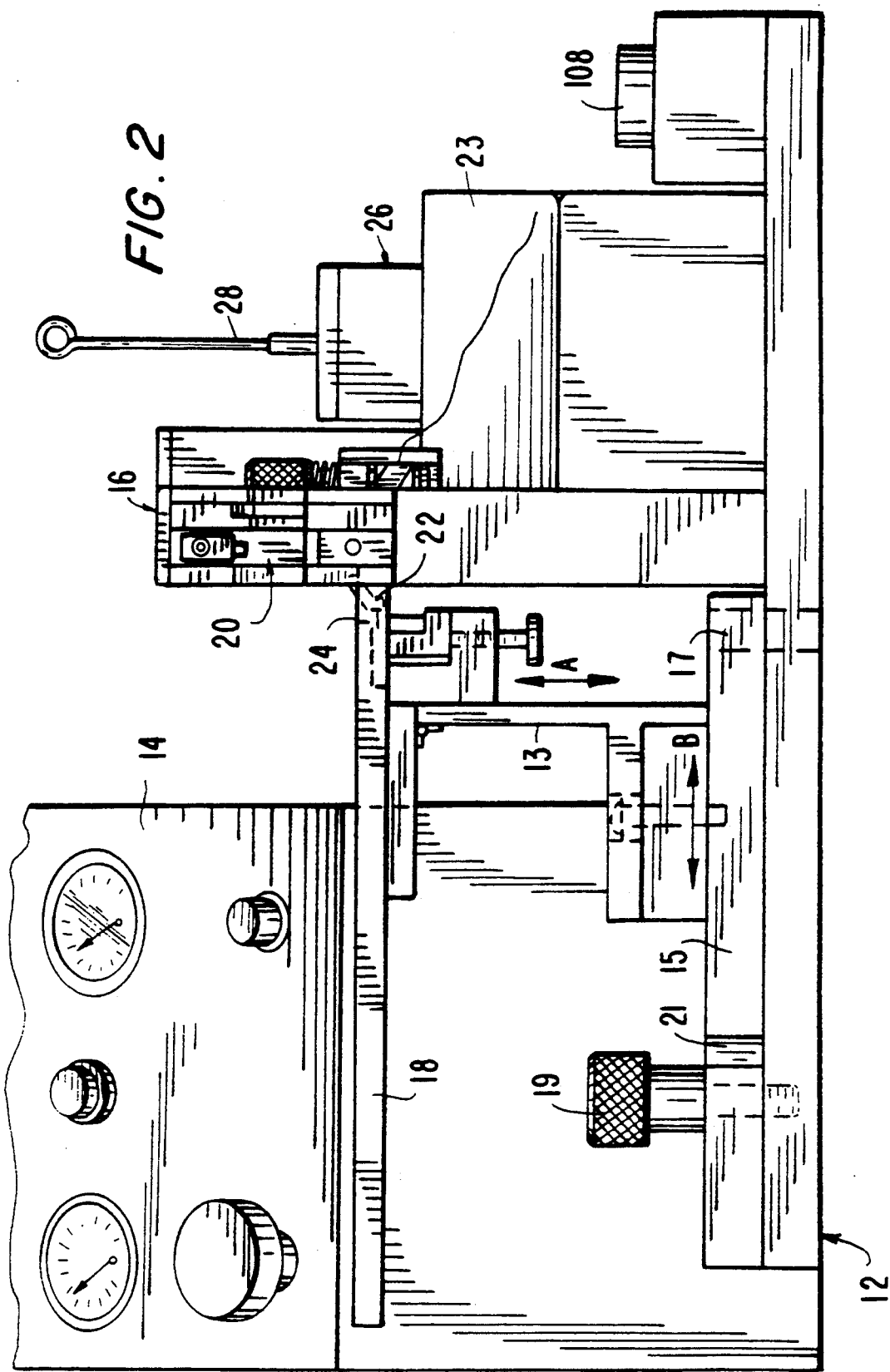
FIG. 2 is a front elevational view of the suture needle attaching apparatus taken along lines 2—2 of FIG. 1.
Figure 3:
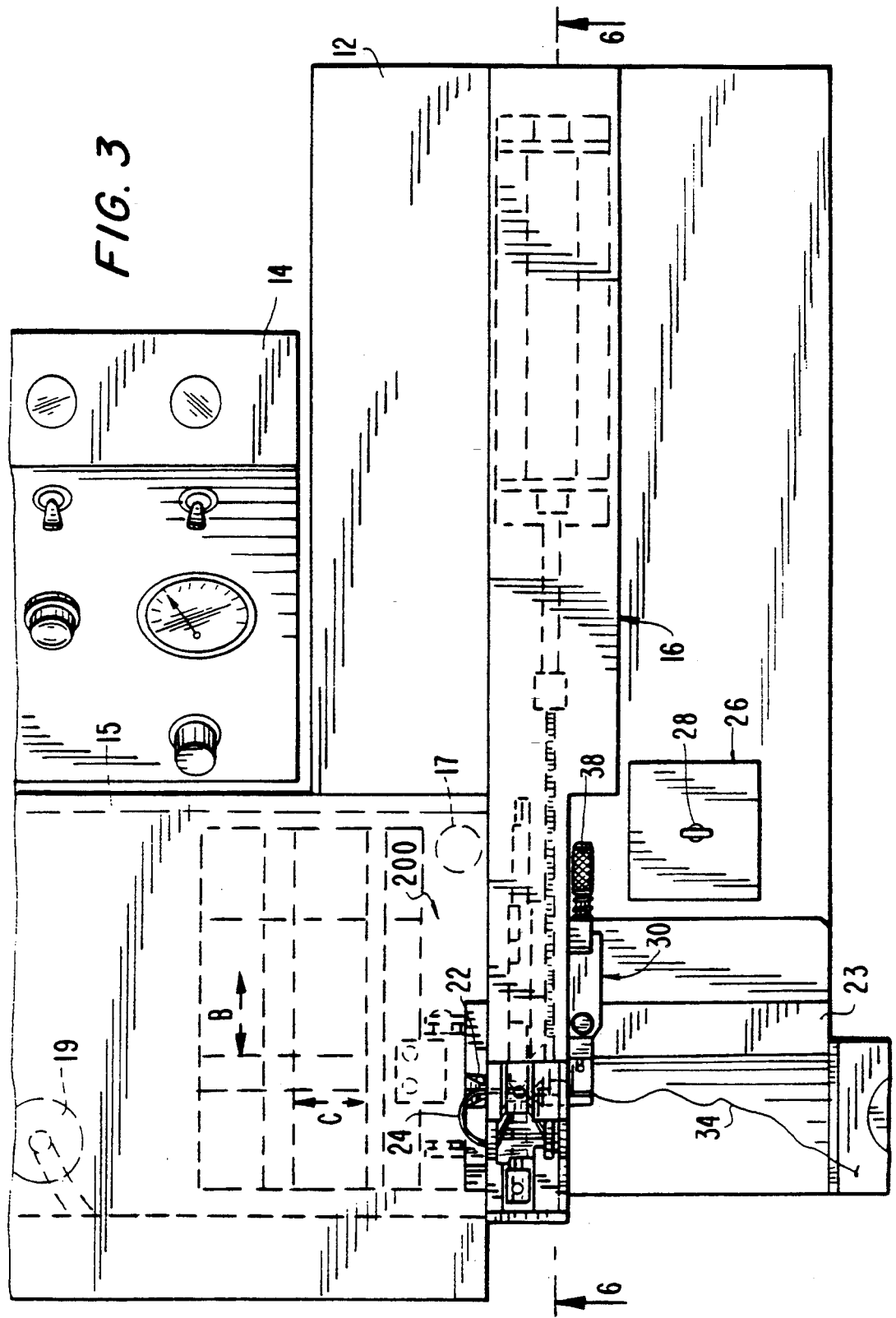
FIG. 3 is a top plan view of the suture needle attaching apparatus taken along line 3—3 of FIG. 1.
Figure 4:
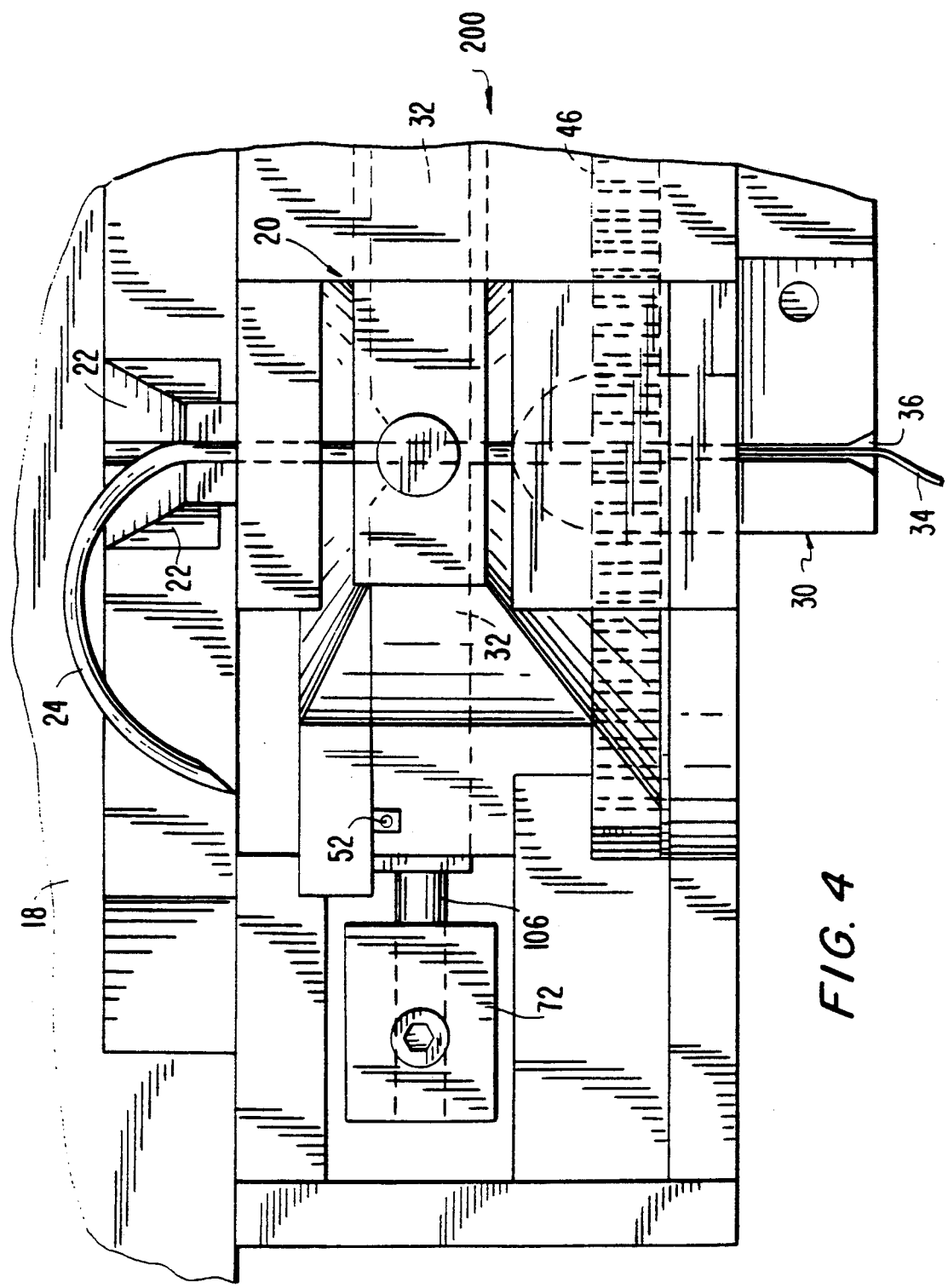
FIG. 4 is an enlarged top plan view of the crimping zone of the apparatus of FIG. 1.

Referring now to FIGS. 2-4, frame 12 further includes horizontal support table 18 which is provided to support the needle 24 and is adjustable in three directions of a three-dimensional coordinate system, as shown by arrows A, B and C. For example, as viewed in FIG. 1, direction "A" represents vertical movement, direction "B" represents fore and aft movement and direction "C" represents lateral (i.e., left and right) movement.

Referring once again to FIGS. 2-4, table 18 rests on vertical bracket 13 and the bracket rests on support base 15. Support base 15 is pivotally mounted to frame 12 by pivot pin 17 to provide pivotal movement of table 18, bracket 13 and support base 15. Thumb screw 19 secures support base 15 to frame 12 so that table 18 is maintained in a fixed relation to the frame. Loosening of thumb screw 19 permits free pivotal movement of table 18 with respect to frame 12. Such pivotal movement permits access to the die rotating and crimping system 16 to facilitate ease of removal or insertion of die cartridge 20 into the die rotating and crimping system 16. Needle grippers 22, best shown in FIG. 4, are secured to table 18, adjacent die cartridge 20 so that when needle 24 is positioned between needle grippers 22 the needle will automatically become aligned with the working surface of the crimping dies as shown in crimping area 200 of FIGS. 3 and 4. Preferably, needle grippers 22 are pneumatic jaws controlled by control panel 14 as will be described in further detail below. Hand rest 23 is secured to frame 12 adjacent die cartridge 20 and provides the operator with an ergonomic hand rest when inserting sutures into the needle and when operating the apparatus of the present invention.

Referring again to FIG. 1, emergency stop switch 26 is secured to frame 12 and is provided to terminate the power to the active components of the apparatus and prevent further actuation thereof. Preferably, emergency stop switch 26 is positioned in close proximity to die cartridge 20, as shown in FIG. 1, so as to enable the operator to quickly move arm 28 of emergency switch 26 with fingers to shut down of the system in the event of an emergency.

Figure 5:
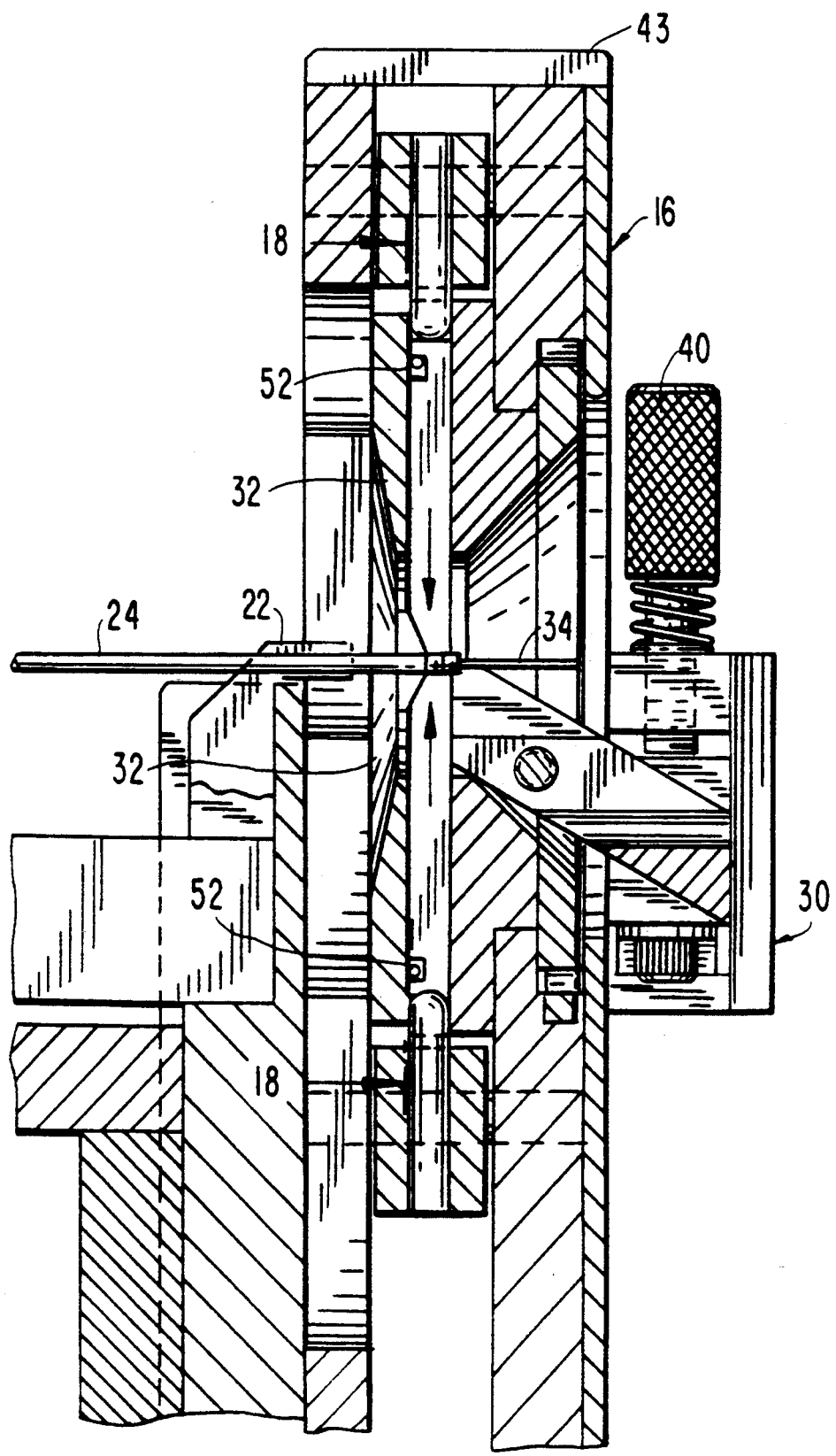
FIG. 5 is a front elevational view of the suture needle attaching apparatus taken along lines 5—5 of FIG. 1, illustrating the dies rotated 90° and the needle positioned for crimping.

Referring now to FIGS. 4 and 5, enlarged views of the needle crimping zone are illustrated. Guide member 30 is secured to die rotating and crimping system 16 adjacent die cartridge 20 to perform two functions. First, guide member 30 includes channel 36, shown in FIG. 4, to guide suture 34 into an appropriately dimensioned opening in the end face of needle 24. Second, guide member 30 is a stop member which limits the positioning of needle 24 between dies 32 so that the dies crimp the needle at a point where suture 34 will be engaged or crimped by the deformed surface of the needle. Preferably, guide member 30 is adjustable in the horizontal direction via adjusting screw 38, shown in FIG. 3, and the vertical direction via adjusting screw 40, shown in FIG. 5.

Figure 6:
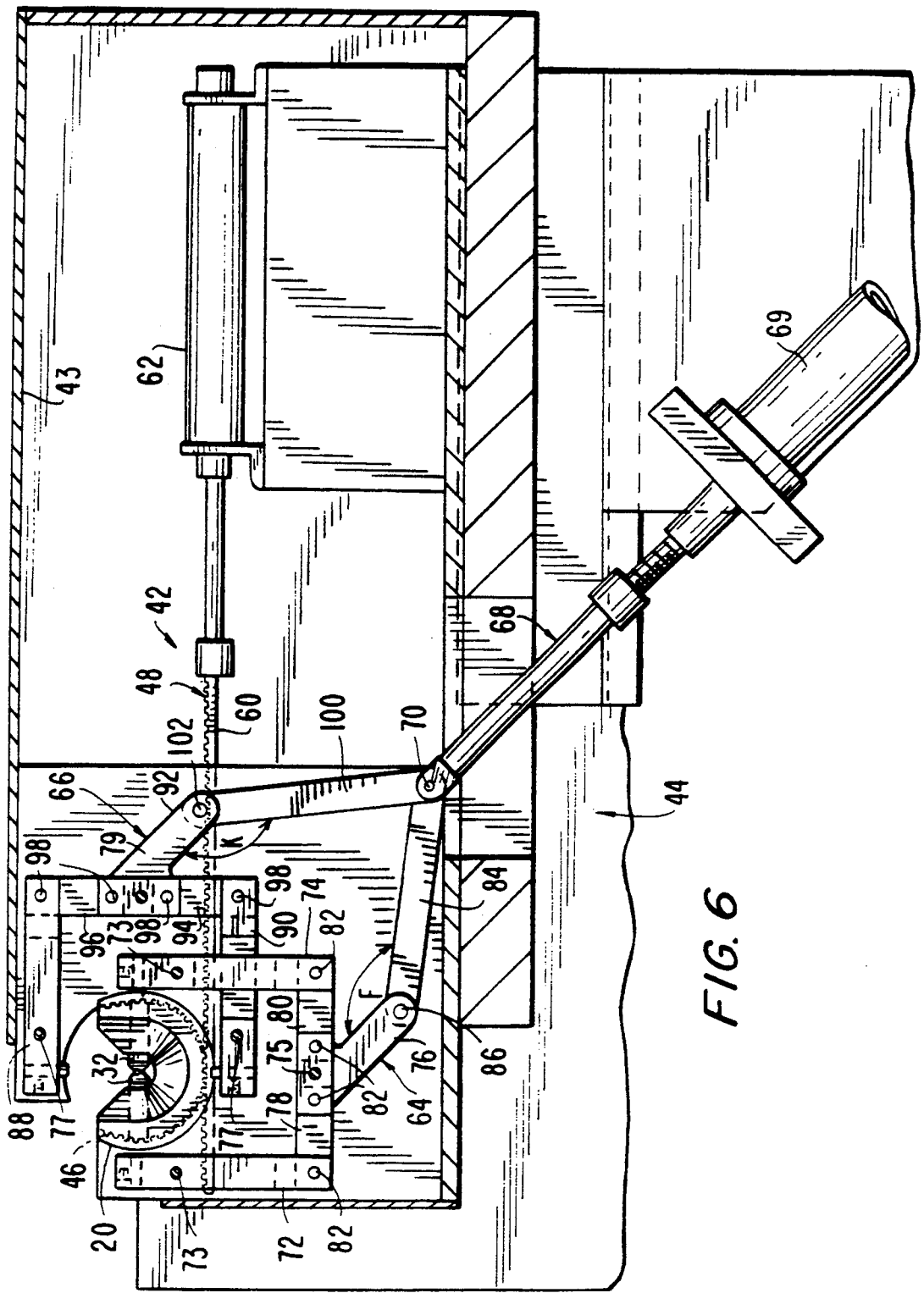
FIG. 6 is a side elevational view of the rotating and crimping system associated with the suture needle attaching apparatus of the present invention.
Figure 7:
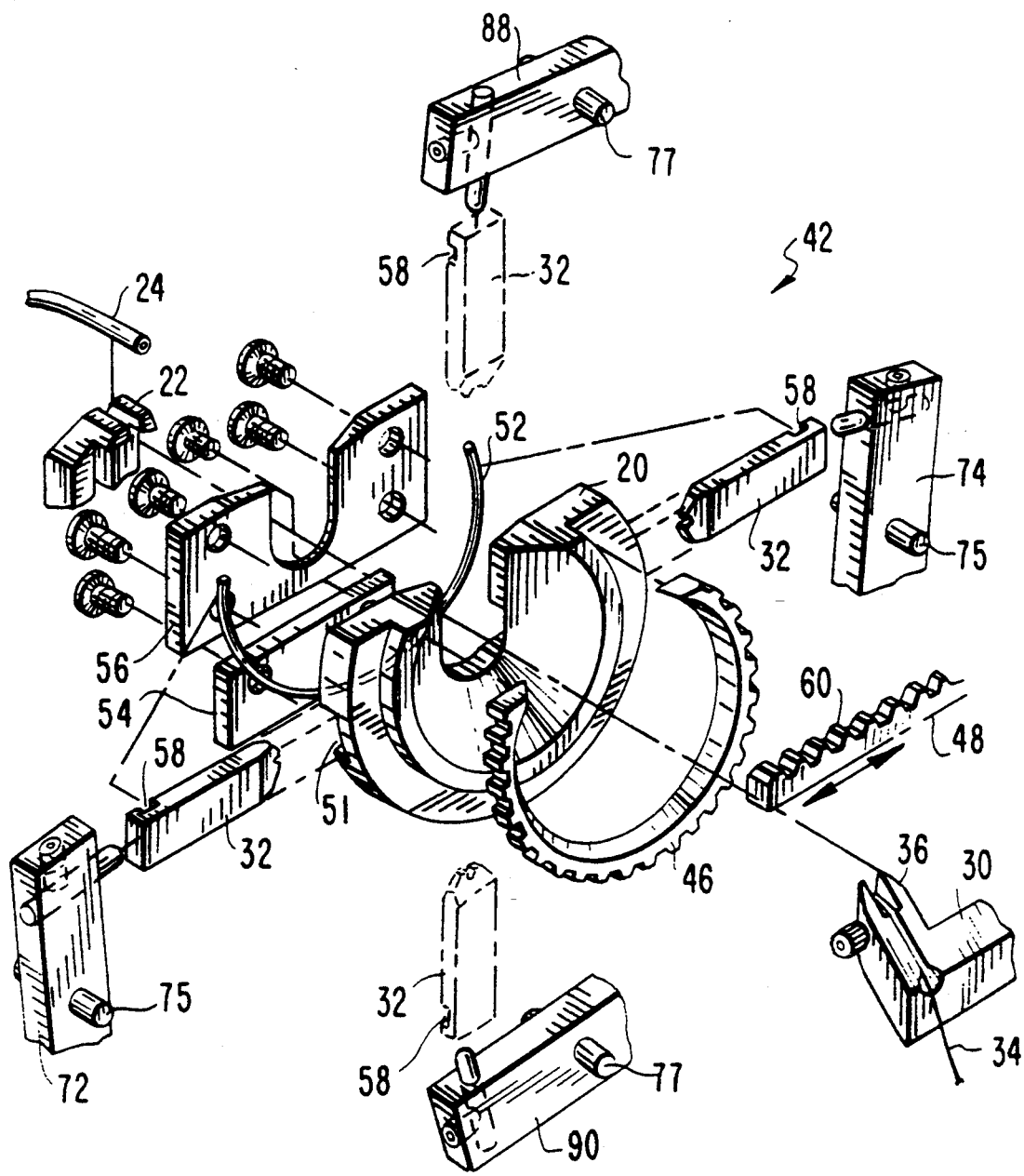
FIG. 7 is an enlarged perspective view with parts separated of a portion of the rotating and crimping systems of FIG. 6.
Figure 8:
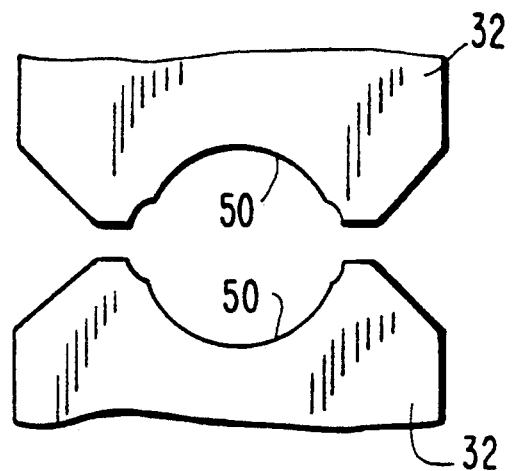
FIG. 8 is a plan view of a portion of the dies of the crimping system of FIG. 6, illustrating a "lap-overlap" die configuration.
Figure 9:
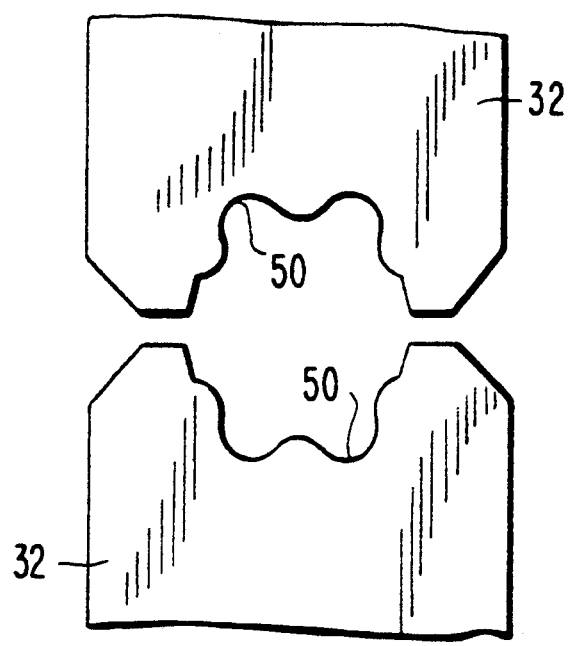
FIG. 9 is a plan view of a portion of an alternative embodiment of the crimping system of FIG. 6, illustrating a "clover leaf" die configuration.

Referring now to FIGS. 6-9, the rotating and crimping system 16 of the present invention will now be described. Rotating and crimping system 16 includes a rotating portion 42 and a crimping portion 44, both of which are positioned within housing 43, as shown in FIG. 6. As shown in FIGS. 6 and 7, rotating portion 42 generally includes a pair of needle crimping dies 32, rotating die cartridge or member 20, pinion gear 46 secured to die cartridge 20 and rack gear 48 which engages pinion gear 46 so as to translate linear movement of rack gear 48 to rotational movement of die cartridge 20. The working surface 50 of each die 32 is preferably the "lap-overlap" type, shown in FIG. 8. However, the working surface 50 of each die may be of the "clover leaf" type, shown in FIG. 9, the staking type (not shown) or the like. One example of a clover leaf die of this type is described in commonly assigned U.S. Pat. No. 5,099,676 to Proto et al. Another example of a preferred die configuration is illustrated in U.S. Pat. No. 5,046,350 to Proto et al.

Figure 10:
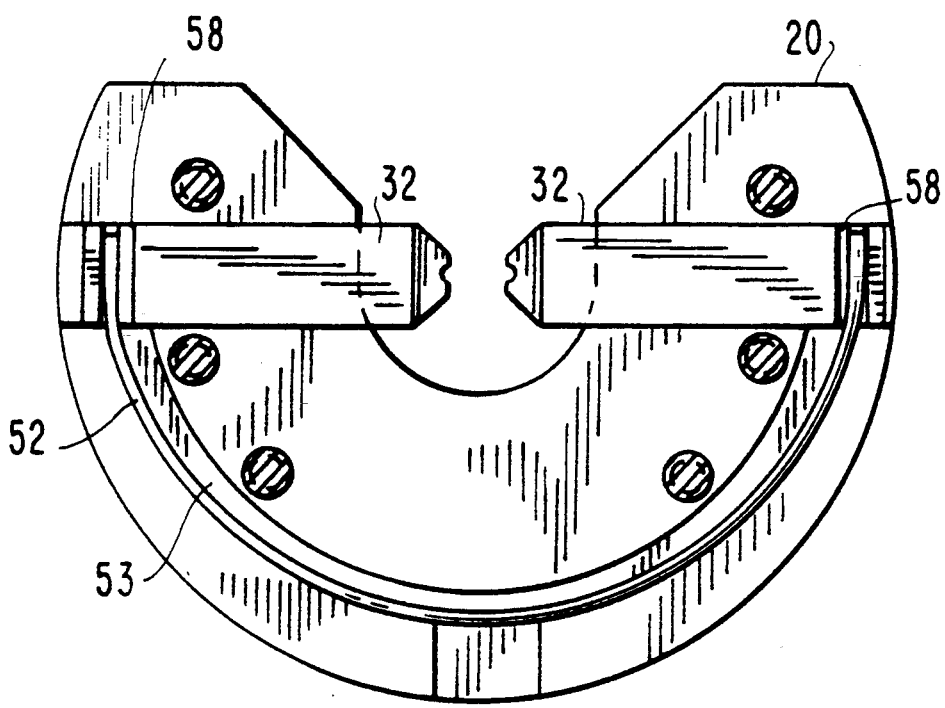
FIG. 10 is a side elevational view of a portion of the die cartridge shown in FIG. 7, illustrating the sliding relationship between the die cartridge and the dies.

Referring again to FIGS. 6–7, dies 32 are positioned on die cartridge 20 such that the working surface 50 of each die 32 oppose each other and at least one of the dies is slidably secured thereto. Preferably, both dies are positioned within channels 51 in the form of die cartridge 20 and are slidably retained therein, as shown in FIG. 7. Arcuate spring 52 in the form of a large circlip as shown, is positioned within arcuate channel 53 of die cartridge 20 so that each end portion of arcuate spring 52 engages a corresponding die channel 58 in each die 32, as shown in FIG. 10. The dies 32 and arcuate spring 52 are then secured to die cartridge 20 by removable plates 54 and 56. In this configuration, spring 52 normally biases dies 32 in directions away from the center of die cartridge 20.

Referring to FIG. 6, rotating portion 42 is shown. Rack gear 48 includes gear section 60 attached to linear drive section 62. Gear section 60 of rack gear 48 is configured to engage pinion gear 46, as mentioned above. Preferably, linear drive section 62 is a pneumatic pump which is controlled by control panel 14, as will be discussed hereinbelow. However, drive section 50 may be any known drive system, such as an electric motor or hydraulic pump.

Continuing to refer to FIG. 6, the crimping portion 44 will now be described. Crimping portion 44 includes a pair of crimping arms 64 and 66 which are pivotally secured to crimping drive member 68 by pin 70. Each crimping arm is substantially identical and provided to selectively cause dies 32 to bias toward the center of die cartridge 20. Crimping arm 64 includes a pair of lever arms 72 and 74 which are pivotally connected to pivot arm 76 via cross-bars 78 and 80 and pins 82. In addition, securing pins 73, positioned on the upper portion of lever arms 72 and 74, and securing pin 75 positioned on pivot arm 76 are provided to maintain lever arms 72 and 74 in a fixed pivotal relationship within housing 43. This relationship is maintained such that lever arms 72 and 74 and cross bars 78 and 80 form a "U" shaped chamber to partially receive die cartridge 20, as shown in FIG. 6. Pivot arm 76 is also pivotally secured to articulating arm 84 by pin 86, and articulating arm 84 is secured to crimping drive member 68 by pin 70.

Similarly, crimping arm 66 includes a pair of lever arms 88 and 90 which are pivotally connected to pivot arm 92 via cross-bars 94 and 96 and pins 98. In addition, securing pins 77, positioned on the upper portion of lever arms 88 and 90, and securing pin 79 positioned on pivot arm 92 are provided to maintain lever arms 88 and 90 in a fixed pivotal relationship within housing 43 so that lever arms 88 and 90 and cross-bars 94 and 96 form a "U" shaped chamber to partially receive die cartridge 20, as shown in FIG. 6.

Preferably, lever arms 88 and 90 are positioned about the die cartridge 90° out of phase from lever arms 72 and 74 as shown. This configuration provides uniform crimping of suture 34 to needle 24. Pivot arm 92 is also pivotally secured to articulating arm 100 by pin 102 and articulating arm 100 is pivotally secured to crimping drive member 68 by pin 70. Also, preferably, crimping drive member 68 is connected to a pneumatic pump 69 as shown, which is operator controlled at control panel 14, as will be discussed below. However, crimping drive member 68 may be connected to any other known type of drive system, such as an electric motor or a hydraulic pump, etc.

The operation of the apparatus of the present invention will now be described with particular reference to FIGS. 11–20 in conjunction with FIGS. 1–6. Generally, when the dies are in the crimping position pneumatic pump 69 causes crimping drive member 68 to be located at the center of its stroke. When the dies are in the open position crimping drive member 68 is at either the extended or retracted end of its stroke as determined by pneumatic pump 69.

Figure 11:
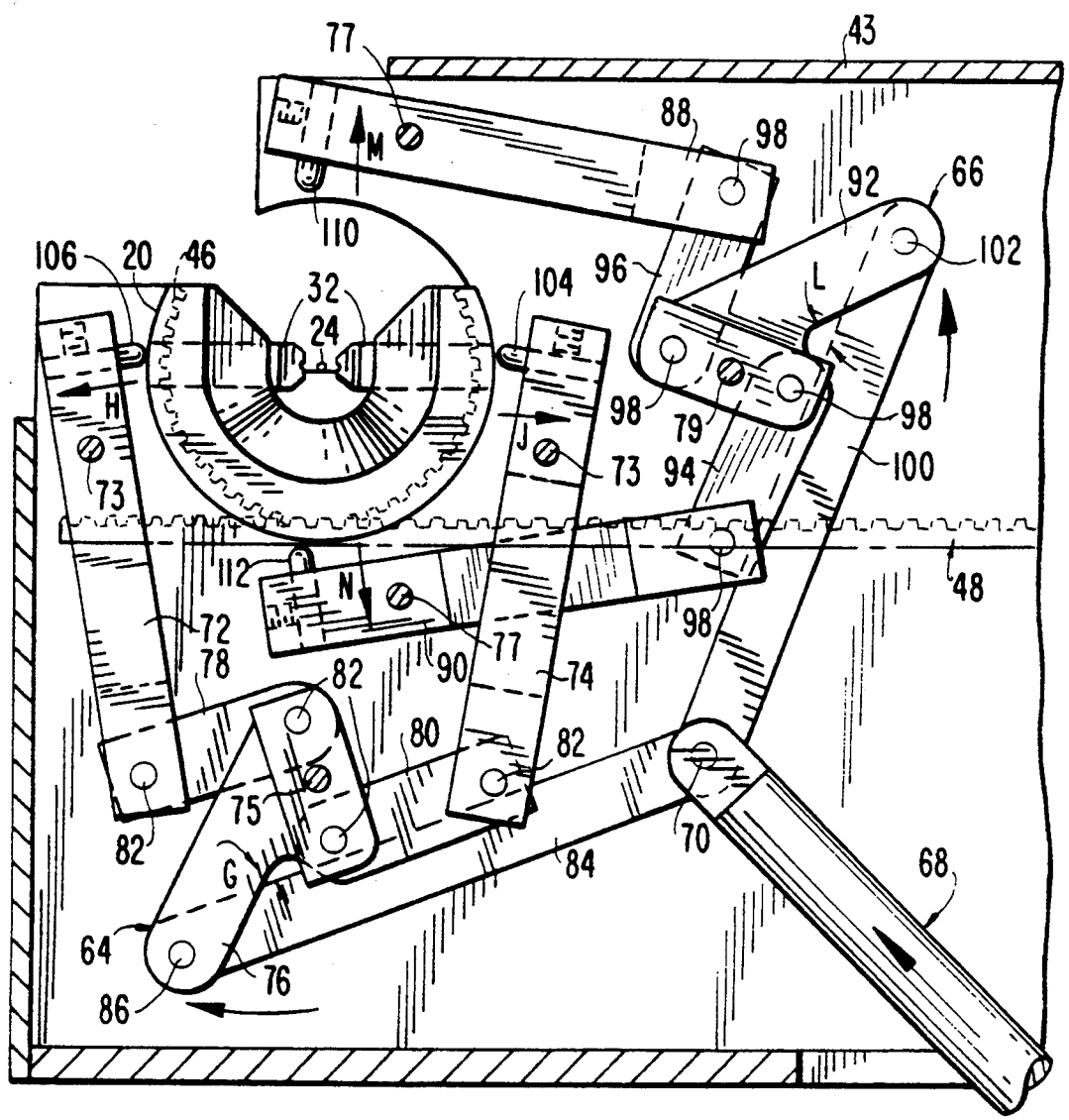
FIG. 11 is a side elevational view of a portion of the rotating and crimping systems of FIG. 6, illustrating the die cartridge in a normal position and the dies in an open position.

Referring now to FIG. 11, initially die cartridge 20 is positioned in the normal position, i.e., crimping drive member 68 is at the extended end of the stroke and dies 32 are in the open position and horizontally orientated as shown. However, depending upon the desired sequence, crimping drive member 68 could initially be at the retracted end of the stroke when in the normal position. As mentioned above, securing pins 73, 75, 77 and 79 maintain each corresponding pair of lever arms in a fixed pivotal relationship within housing 43, thus, when the stroke of crimping drive member 68 moves toward the extended end, shown by arrow E, articulating arm 84 pivots causing pivotal movement of pivot arm 76 about securing pin 75 via pin 86. As a result, obtuse angle "F", shown in FIG. 6, is decreased to acute angle "G", shown in FIG. 11. The described pivotal motion of pivot arm 76 causes lever arms 72 and 74 to pivot away from the center of die cartridge 20, shown by arrows "H" and "J", in response to pivotal movement of cross bars 78 and 80. Similarly, articulating arm 100 pivots in response to the above described motion of crimping drive member 68, causing pivot arm 92 to pivot about securing pin 79 via pin 102. As a result, obtuse angle K, shown in FIG. 6, is decreased to acute angle L, shown in FIG. 11. The described pivotal motion of pivot arm 92 causes lever arms 88 and 90 to pivot away from the center of die cartridge 20, shown by arrows M and N, in response to pivotal movement of cross-bars 94 and 96. As a result of the movement by lever arms 72 and 74 away from the center of die cartridge 20, pusher pins 104 and 106 disengage dies 32 so as to allow dies 32 to bias towards their normal position in response to arcuate spring 52, as noted above.

Figure 12:
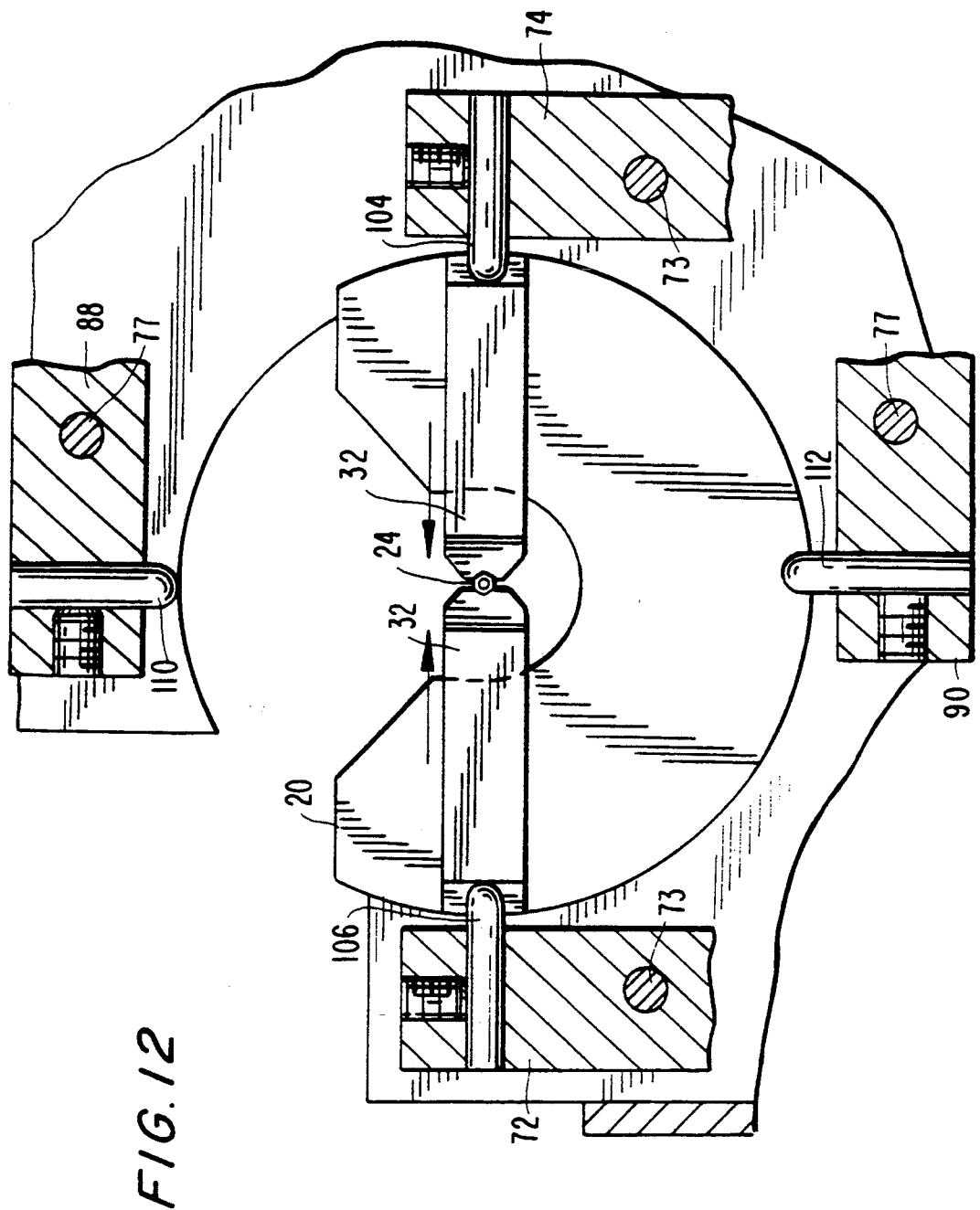
FIG. 12 is a side elevational view, greatly enlarged, of the die cartridge of FIG. 11, illustrating the dies in a preset position.

When dies 32 are in the open position, the operator inserts a needle 24 between dies 32 until the needle face abuts guide member 30, as shown in FIG. 5. The operator then activates control panel 14 so that dies 32 and needle grippers 22 are respectively set to a preset position. To activate control panel 14, a center pivot foot pedal (not shown) may be utilized which will set dies 32 and needle grippers 22 to the preset position when tilted in one direction and activate the crimping cycle when tilted in the other direction. As shown in FIG. 12, the preset position is the position where dies 32 grasp needle 24 with a force, exerted by pusher pins 104 and 106, sufficient to maintain needle 24 therebetween without substantially deforming the needle. The preferred force is about 10 psi. Either simultaneously with the preset gripping by dies 32 or after a time delay of approximately two seconds, needle grippers 22 also grasp needle 24 to maintain the position of the needle during the crimping cycle of the apparatus, as shown in FIGS. 3 and 4. Reset switch 108 is provided to allow the operator to reset the crimping system from the preset position by causing control panel 14 to open dies 32 and needle grippers 22 via crimping portion 44. Once in the preset position, a suture 34 is inserted into the needle bore via guide member 30, as described above.

Figure 13:
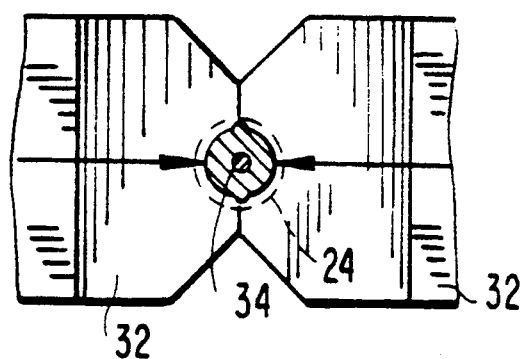
FIG. 13 is a plan view of the dies of FIG. 8 in the normal position and having a crimped needle positioned therebetween.
Figure 14:
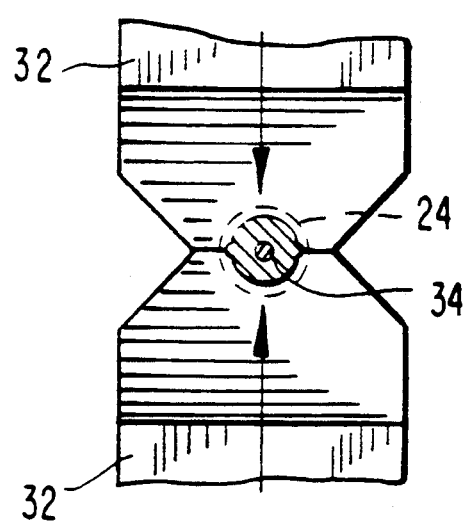
FIG. 14 is a plan view of the dies of FIG. 13, illustrating the dies in a rotated position and the needle crimped therebetween.

After insertion of suture 34 the crimping cycle is activated by control panel 14. As mentioned above, the foot pedal is preferably utilized to activate the crimping cycle. Generally, the crimping cycle includes two steps. The first step crimps the needle on two sides and the second step rotates the dies and crimps the needle on two sides which are out of phase with the sides originally crimped, as shown in FIGS. 13 and 14. Preferably, the second crimping action is 90° out of phase with the first crimping action to ensure a uniform attachment of the suture to the needle. It should be noted that for each part of the crimping cycle the dies are caused to impact the needle twice so as to ensure sufficient and uniform crimping of the suture within the needle bore.

Figure 15:
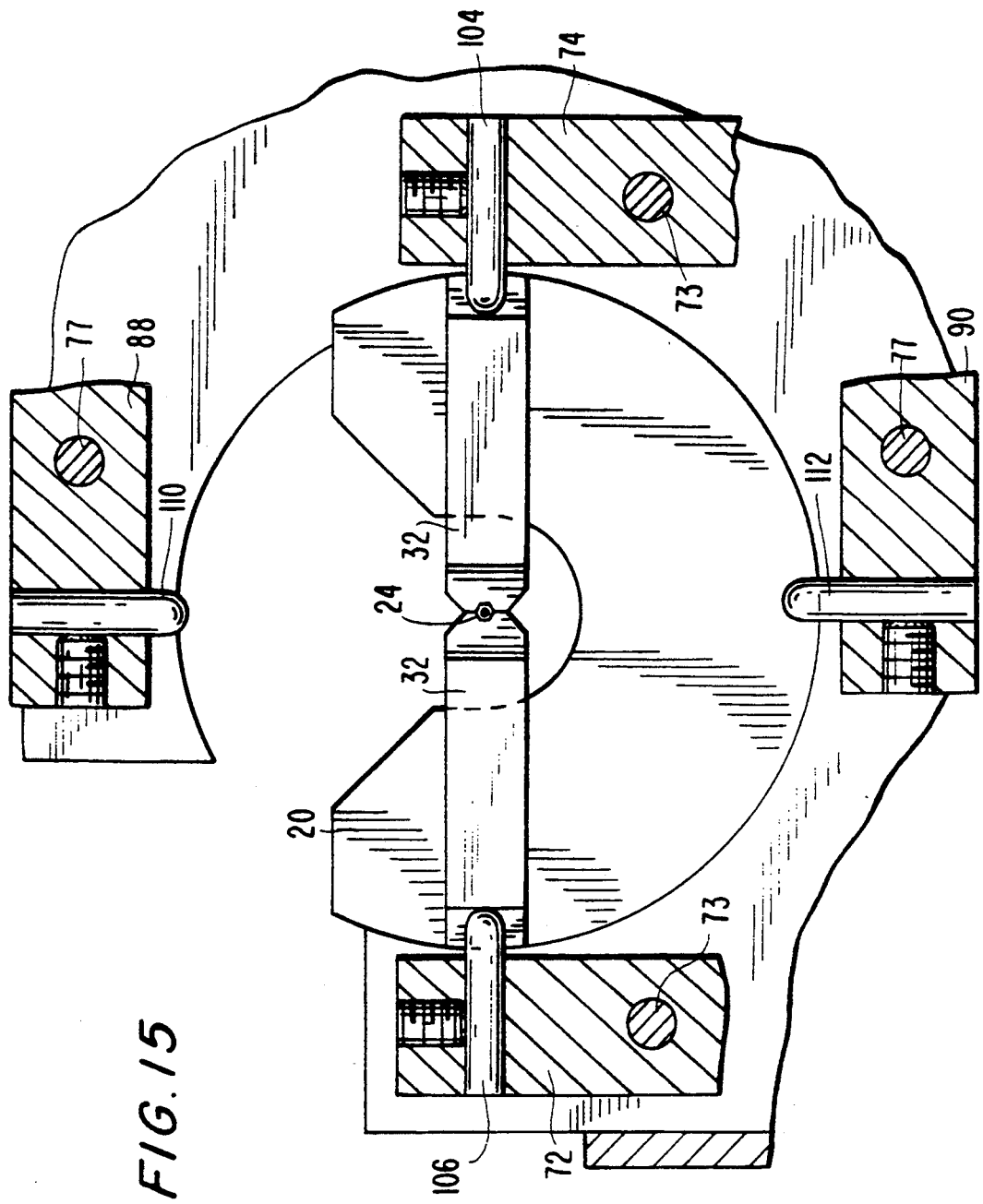
FIG. 15 is a side elevational view, greatly enlarged, of the die cartridge of FIG. 11, illustrating the dies in a crimping position.

Referring to FIGS. 11 and 15, the first step of the crimping cycle causes crimping drive member 68 to move towards the center of the stroke so that pusher pins 104 and 106 bias dies 32 towards needle 24 sufficiently to deform the needle surface with the working surface of each die and secure suture 34 thereto. Preferably, the force applied to deform needle 24 by pusher pins 104 and 106 is between about 40 psi and about 80 psi. After deforming the needle surface, the dies are caused to return to the open position shown in FIG. 11 by moving crimping drive member to either the extended or retracted end of the stroke as described above.

Once the first part of the crimping cycle is completed the apparatus automatically rotates die cartridge 20 so that each die 32 is shifted a predetermined distance from their normal position, preferably about 90°. As previously mentioned, rotational movement of die cartridge 20 occurs when linear drive section 62, shown in FIG. 6, retracts gear section 48, shown by arrow P in FIG. 16.

Figure 16:
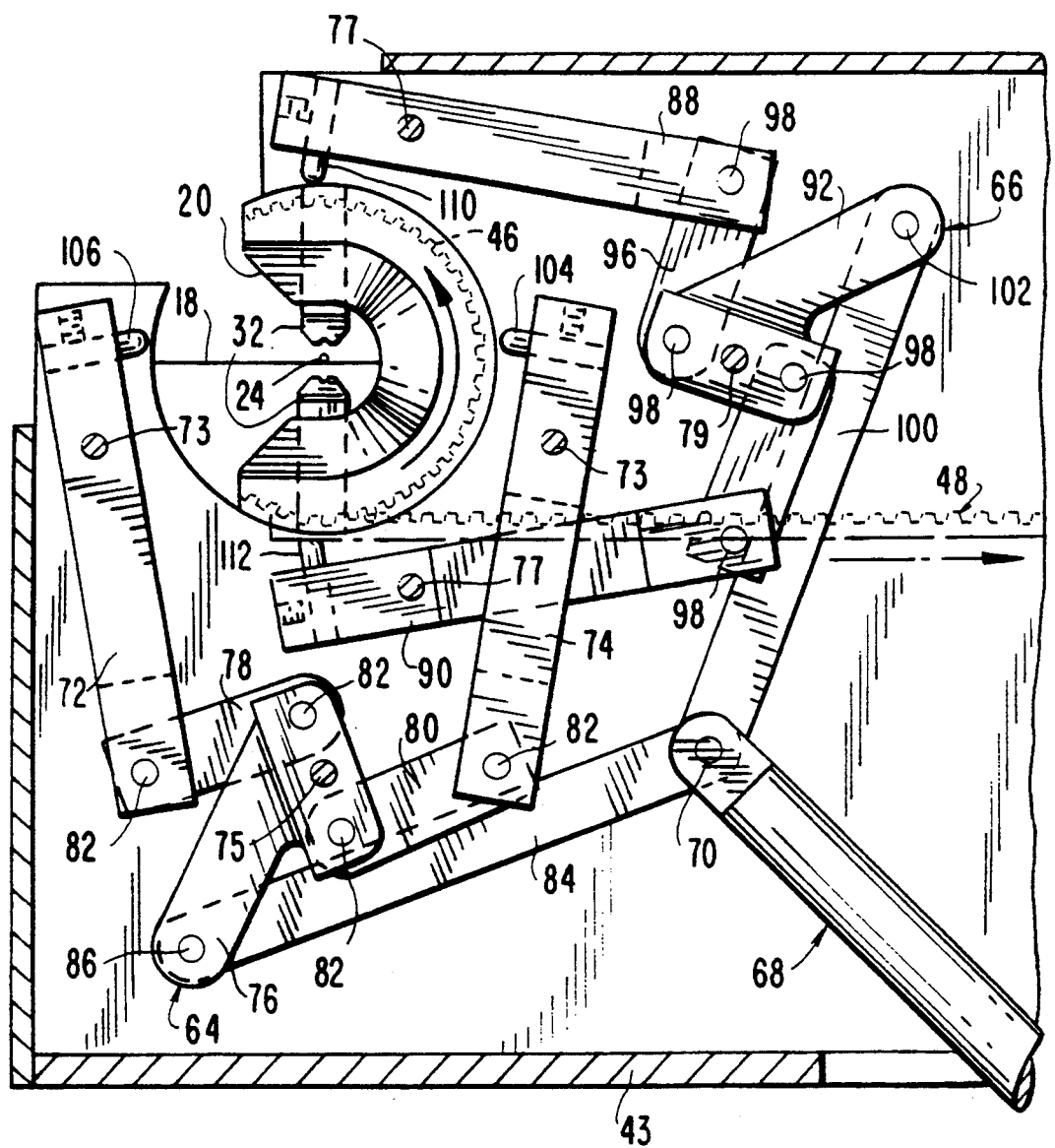
FIG. 16 is a side elevational view similar to FIG. 11, of the rotating and crimping system, illustrating the die cartridge in a rotated position and the dies in an open position.
Figure 17:
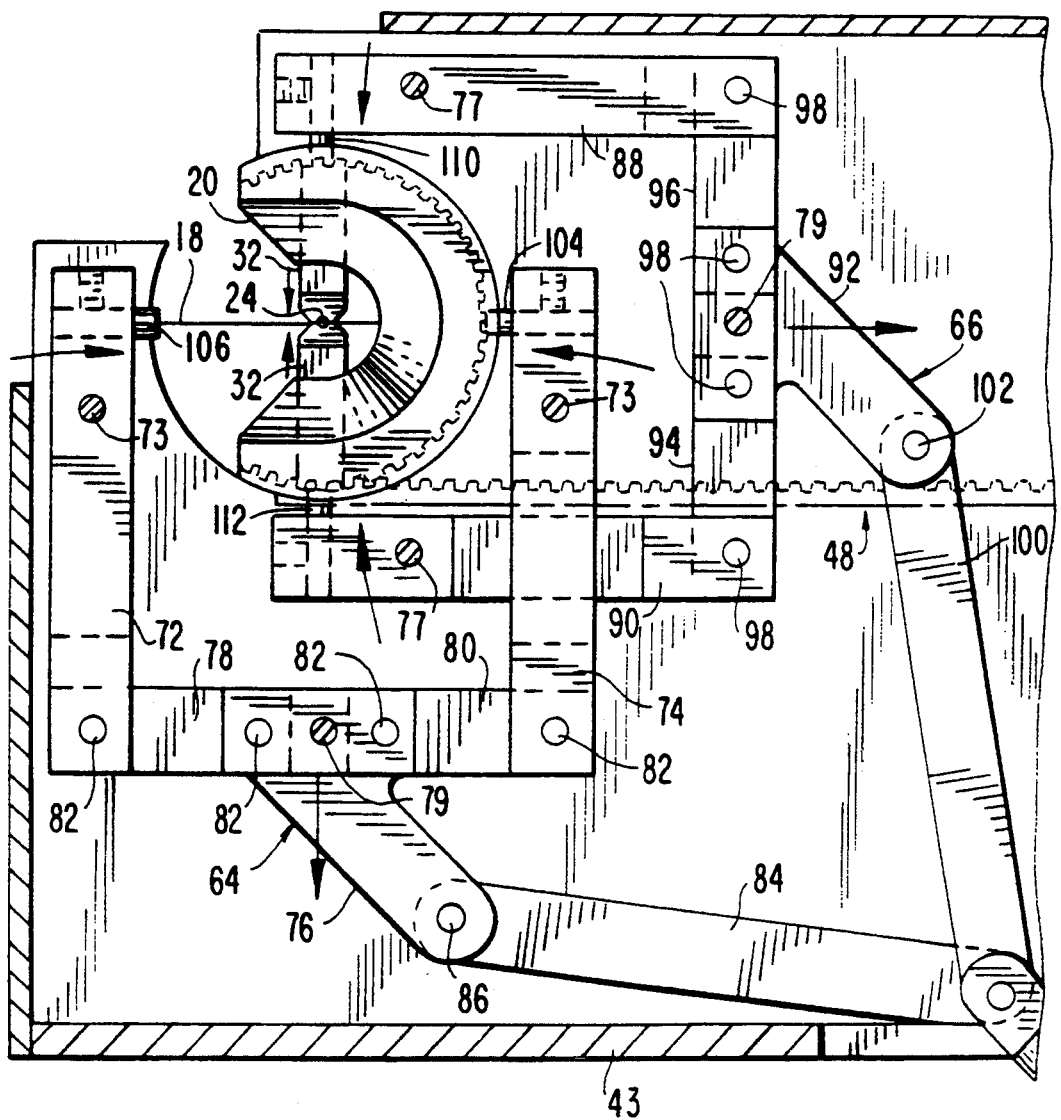
FIG. 17 is a side elevational view of the rotating and crimping systems of FIG. 16, illustrating the dies in a crimping position.
Figure 18:
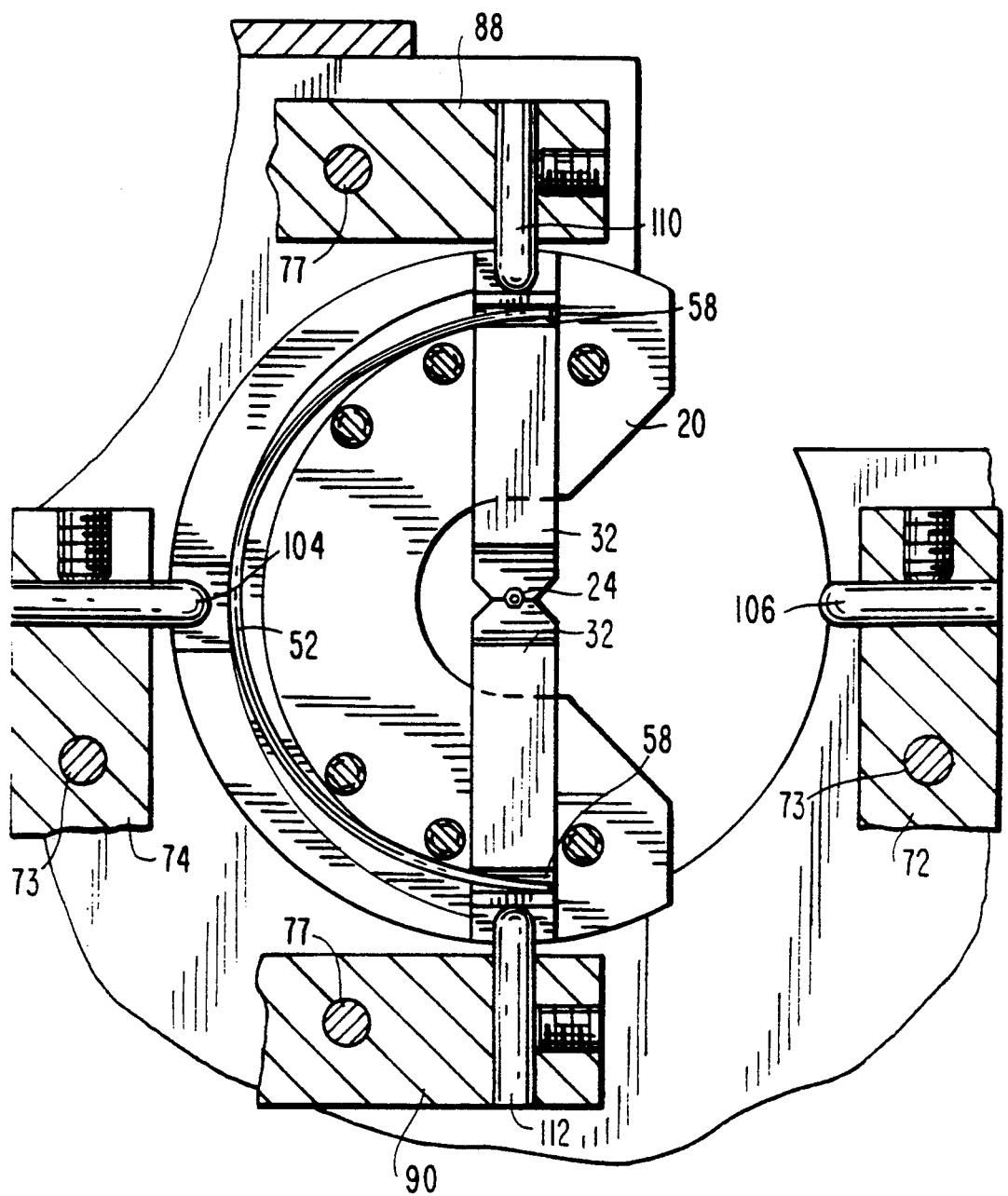
FIG. 18 is a side elevational view of the die cartridge taken along lines 18—18 of FIG. 5 illustrating the dies in a crimped position.
Figure 19:
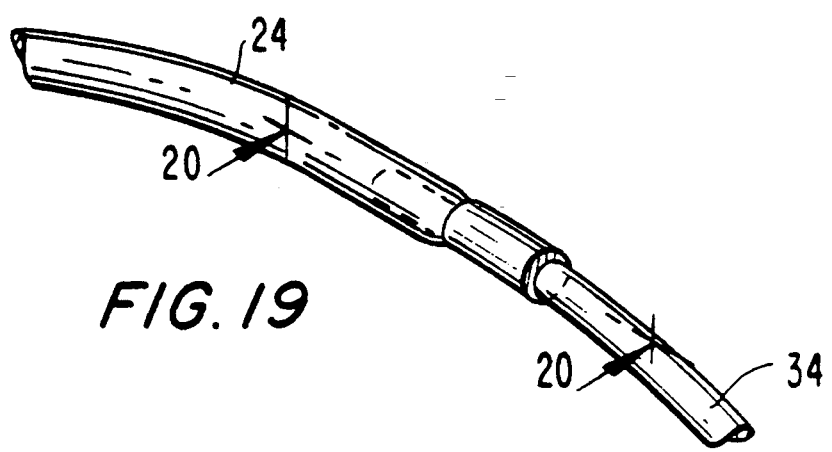
FIG. 19 is a perspective view of a portion of a surgical suture crimped to a surgical needle.
Figure 20:
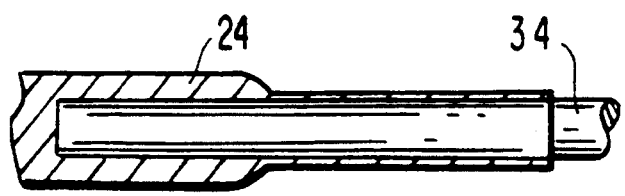
FIG. 20 is a partial cross-sectional view of the crimped surgical suture taken along lines 20—20 of FIG. 19.
Figure 21:
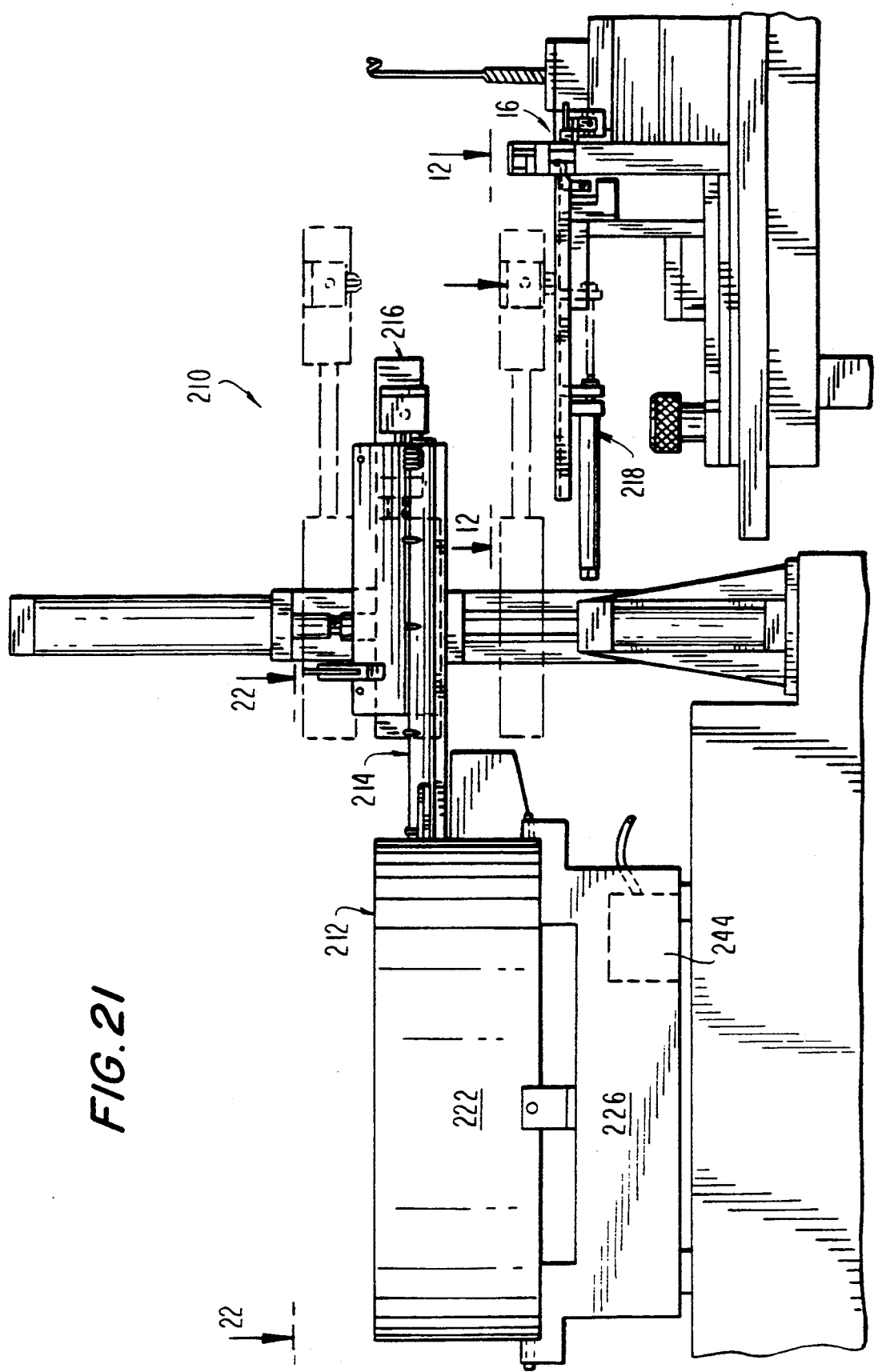
FIG. 21 is a front plan view of the needle presenting system of the present invention, illustrating a needle bowl, a rail feeding system, a pick and place system and a needle pusher system.

Referring now to FIGS. 17 and 18, after rotating die cartridge 20, crimping portion 44 is again activated so that pusher pins 110 and 112 bias dies 32 towards needle 24 sufficiently to deform the needle surface with the working surface of each die 32 thus, securing suture 34 to needle 24 in a uniform manner. As mentioned above, it is preferred that for each part of the crimping cycle the needle and suture are impacted twice. After completing the second part of the crimp cycle the dies are again opened by causing crimping drive member 68 to extend or retract to the end of the stroke, as shown in FIG. 16. Once the dies are opened the operator may remove the crimped needle and suture, shown in FIGS. 19 and 20.

The present invention also provides an automatic system which sequentially presents surgical needles to the above described die rotating and crimping system 16 and will be described with reference to FIGS. 21-40. The needle presenting system 210 includes needle bowl 212, rail feeding system 214, pick and place system 216, needle pusher system 218 and control system 220 which in this embodiment, replaces control panel 14 shown in FIG. 1 and described above, provides the electrical and pneumatic controls for die rotating and crimping system 16 and needle presenting system 210. Preferably, control system 220, shown in FIG. 27, is the model FP-324, manufactured by Action Automation and Controls, located at 10 Larsen Way, North Attleboro, Mass. 02763.

Referring to FIGS. 21-25, needle bowl 212 is preferably in the form of a cylinder having ramps secured to or formed on the side wall 222 of bowl 212 and sweeps formed on the base 224 of bowl 212. The ramps and sweeps are configured to properly orientate and feed the needles to rail feeding system 214. Bowl 212 is positioned on vibrating frame 226 which vibrates the bowl sufficiently to cause needles to be dispersed around the bowl and to traverse along the ramp for presentation to rail feeding system 214. As shown in FIG. 22, needle pad 228 is positioned at the center of base 224 of bowl 212 and is provided to reduce the occurrences of needle point damage when placing the needles into the bowl. From needle pad 228 the needles are dispersed throughout bowl 212 by the vibratory action of the bowl so that the needles are adjacent to the side wall of the bowl. The vibratory action of bowl 212 also causes the needles to move around base 224 along sweeps 230 and 232 for proper orientation while substantially avoiding needle point damage. For example, as shown in FIG. 23, sweep 232 orients needles 234 having the curved portion 234a facing the center of the bowl so that curved portion 234a of needle 234 is adjacent to side wall 222 of the bowl.

As noted above and as shown in FIG. 24, the vibration of bowl 212 also causes the needles to proceed along ramp 236 for presentation to rail feeding system 214. Ramp 236 is secured to or formed into side wall 222 so as to form a spiral shaped member and includes upper surface 238 configured to support the needles. Ramp 236 facilitates movement of the needle from base 224 of bowl 212 up along side wall 222 to a position where the needle can be presented to rail feeding system 214. Preferably, as shown in FIG. 22, lower portion 240 of ramp 236 is narrowed at point 242 which causes any needles which may have traversed along ramp 236 with curved portion 234a facing the center of bowl 212 to fall off the ramp back to the bottom of the bowl thereby properly orientating the needles. In this arrangement, the narrowing of ramp 236 allows the weight of the needle barrel to cause the needle to fall off the ramp.

In the preferred embodiment, bowl 212 is an uncoated stainless steel bowl which utilizes a unique construction (e.g., sweeps 230 and 232 and ramp 236) to prevent damage to the needle point while the needles are dispersed within the bowl, traversed along ramp 236 and properly oriented for presentation to rail feeding system 214. However, bowl 212 may be coated with a protective coating, such as polyurethane, to further ensure that the needle points are not damaged.

Referring again to FIG. 21, the vibratory portion of the bowl utilizes a transformer 244 secured to vibrating frame 226 which vibrates the bowl when a voltage is applied to transformer 244. The voltage applied to the transformer may be varied to either increase or decrease the rate of vibration. One skilled in the art would know the various techniques for varying the voltage to transformer 224.

Figure 25:
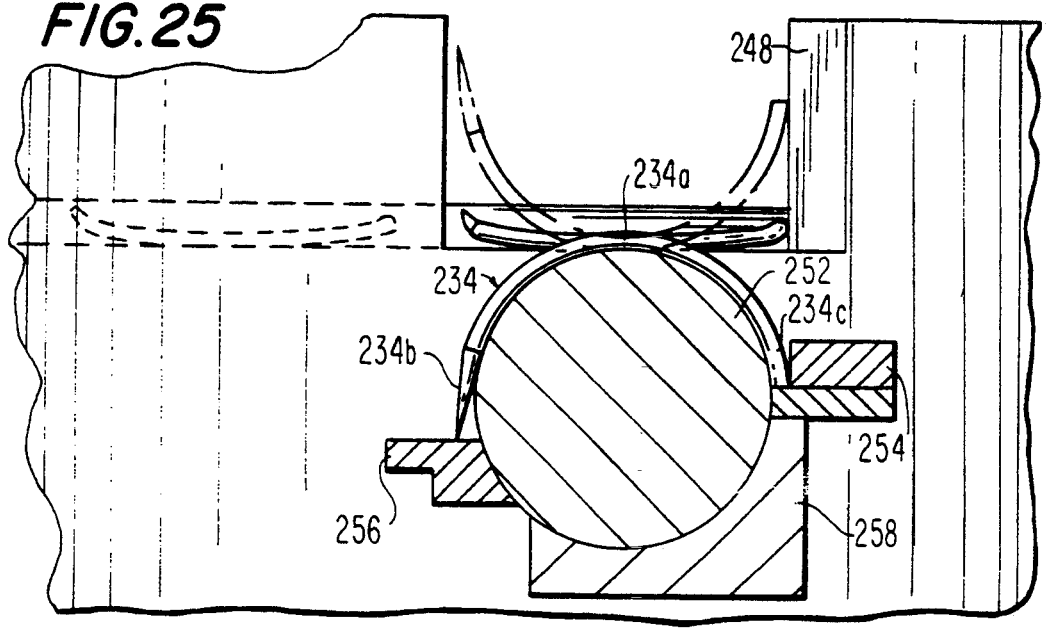
FIG. 25 is a partial cross-sectional view of the rail feeding system of FIG. 22 taken along line 25—25 and illustrating the proper orientation of a needle on the rail feeding system.
Figure 26:
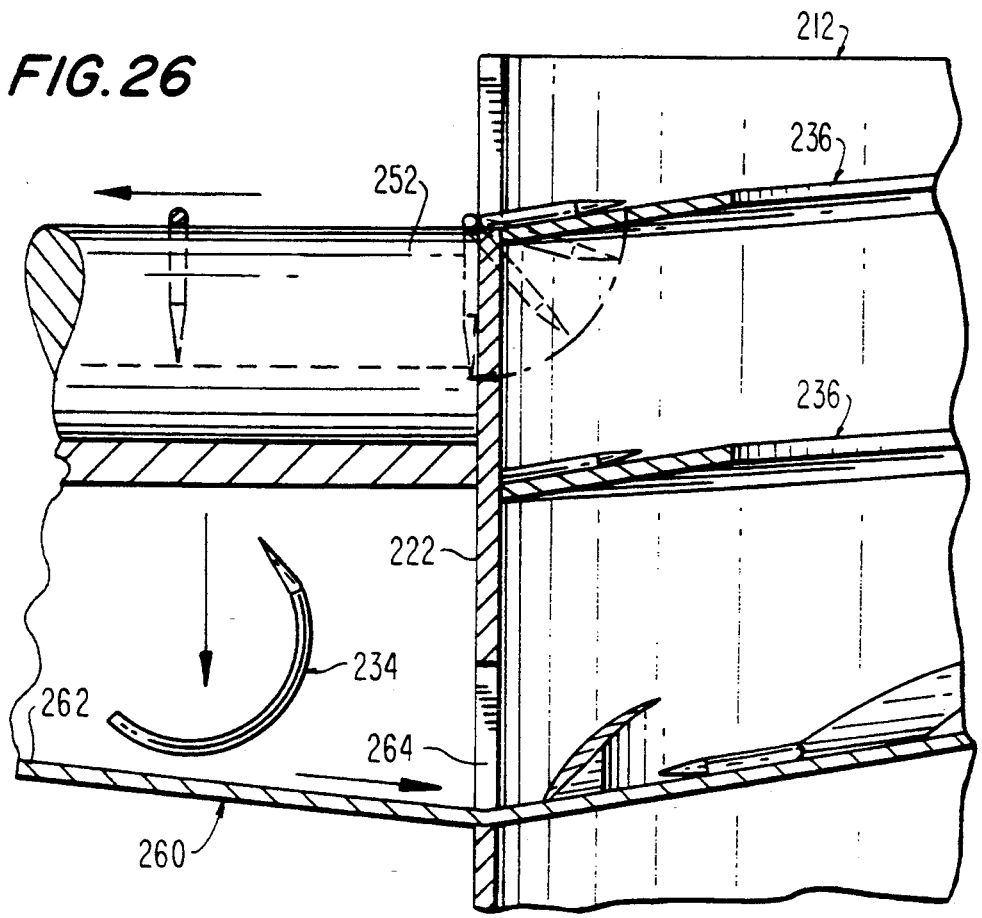
FIG. 26 is a partial cross-sectional view of the needle bowl and the rail feeding system of FIG. 22 taken along line 26—26 and illustrating the motion of a needle during presentation to the rail feeding system.

Referring now to FIGS. 24-27, when the needles reach upper portion 246 of ramp 236 (i.e., the rail presenting position) the needle passes to the rail feeding assembly 214. Further movement of the needle along ramp 236 is prevented by stop 248 (shown in phantom in FIG. 24). Preferably, stop 248 is fabricated from an elastomeric material to prevent damage to the needle, in particular, the needle point. Once at the rail presenting position, the needles pass through opening 250 of side wall 222 onto rail 252, preferably, in a counter-clockwise motion as shown in FIGS. 25 and 26. Needle block 254 and needle guide 256, shown in FIGS. 25 and 27, are secured to rail 252 and/or rail holder 258 and are provided to guide the needle onto the rail without causing damage to the needle point. Preferably needle guide 256 is fabricated from an elastomeric material to minimize damage to the needle point.

Needle block 254 is also provided to properly orient the needles on rail 252 prior to presentation to pick and place system 216. To accomplish this, the weight distribution along the needle is utilized. Typically, the pointed end portion 234b of the needle is lighter then the barrel end portion 234c. Therefore, if the barrel end portion of the needle is oriented against needle block 254 the needle is properly oriented on rail 252 and remains thereon, as shown in FIG. 25. If, however, the needle is presented with barrel end portion 234c facing the side of rail 252 opposite needle block 254, the weight of the barrel forces the needle to rotate counter-clockwise and fall off rail 252, as shown in FIG. 26. Recovery tray 260 is secured to or formed into bowl 252 and is provided to receive the needles which fall off of rail 252. Preferably, recovery tray 260, shown in FIGS. 24 and 26, has bottom surface 262 which is sloped so that needles 234 slide toward opening 264 in side wall 222, shown in FIG. 24, and into bowl 212 for redistribution within the bowl and presentation to rail feeding system 214 in the manner described above. A protective coating, such as polyurethane, may be applied to bottom surface 262 of tray 260 to further minimize needle point damage.

Referring now to FIG. 25, preferably, rail 252 is a cylindrical member which has a radius of curvature that is less than or equal to the radius of curvature of curved portion 234a of needle 234. As a result, when the needles are properly resting on rail 252 as shown in FIG. 25, the needle point portion 234b of the needle is offset from the rail so as to prevent the needle point from engaging the surface of the rail. In typical applications, rail 252 is fabricated from stainless steel, thus if the needle point portion engages or otherwise contacts the hardened surface of the rail, needle point damage may occur. The offset between the needle point and the rail prevents the inadvertent contact therebetween.

Turning to FIG. 27, rail 252 is operatively connected to vibrating transformer 266 via rail holder 258 to cause the needles to sequentially advance along the rail toward a presenting position for pick and place system 216. The rate of vibration of the rail may be varied by adjusting the voltage applied to the transformer. As noted above, one skilled in the art would know the various techniques for varying an applied voltage to increase or decrease the vibration of the rail. In this configuration, multiple needles can be moved along rail 252 and stored thereon until picked or grabbed by pick and place system 216. Photoproximity switch 268 is positioned on support arm 270 and is operatively connected to rail transformer 266 and to bowl transformer 244. Photoproximity switch 260 selectively deactivates the transformer in response to the presence of needles within the activation zone of the photoproximity switch until the needle has advanced past the switch.

Figure 29:
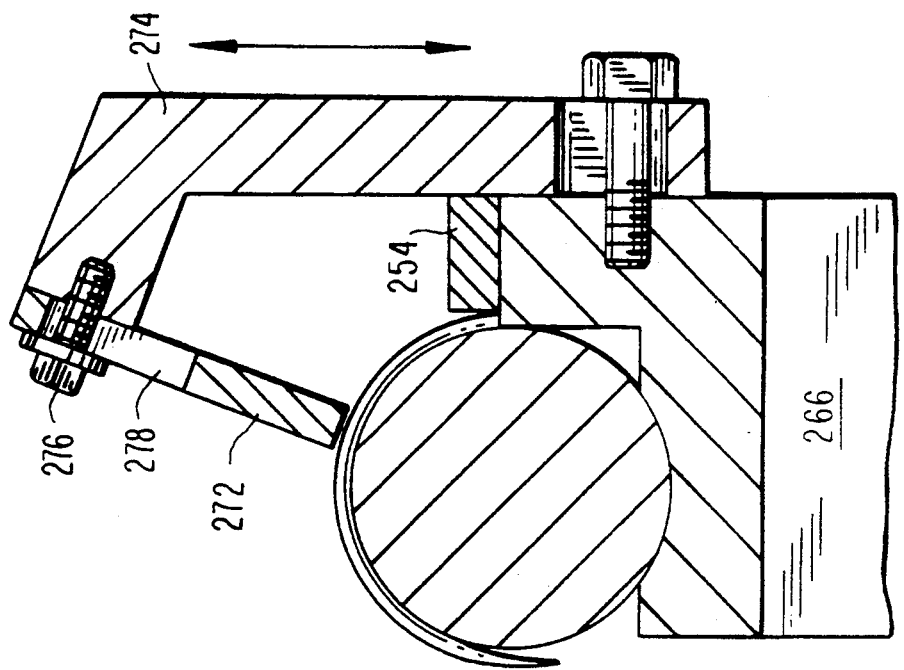
FIG. 29 is a cross-sectional view of the rail feeding system of FIG. 28 taken along line 29—29 and illustrating a needle guide arm which prevents the needle from dislodging from the rail.
Figure 28:
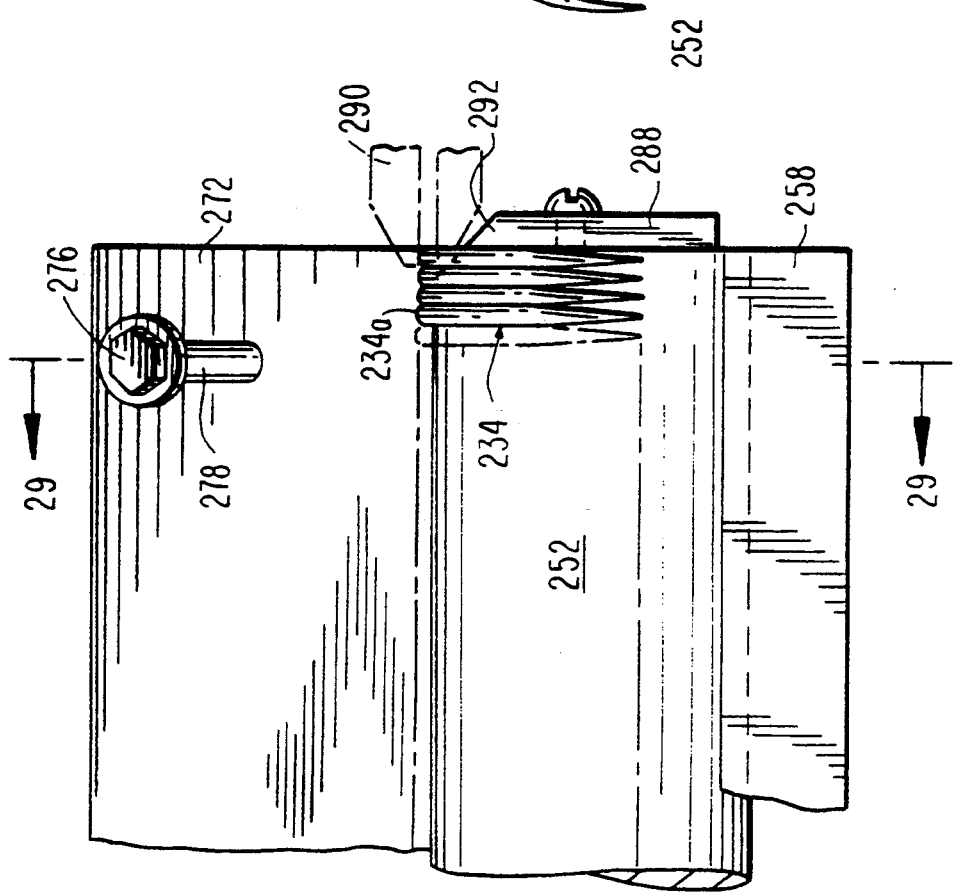
FIG. 28 is a front plan view, greatly enlarged, of a portion of the rail feeding system as a needle is being grabbed by the jaws of the pick and place system.

Referring to FIGS. 28 and 29, needle guide arm 272 is secured to rail holder 258 via guide bracket 274 and is utilized to maintain the needle on rail 252 and prevent needles from becoming dislodged therefrom. Needle guide arm 272 is adjustable so that it can accommodate the various size needle diameters utilized in surgical applications. To adjust guide arm 272, the operator simply loosens bolts 276 and slides the guide arm within slots 278.

Figure 30:
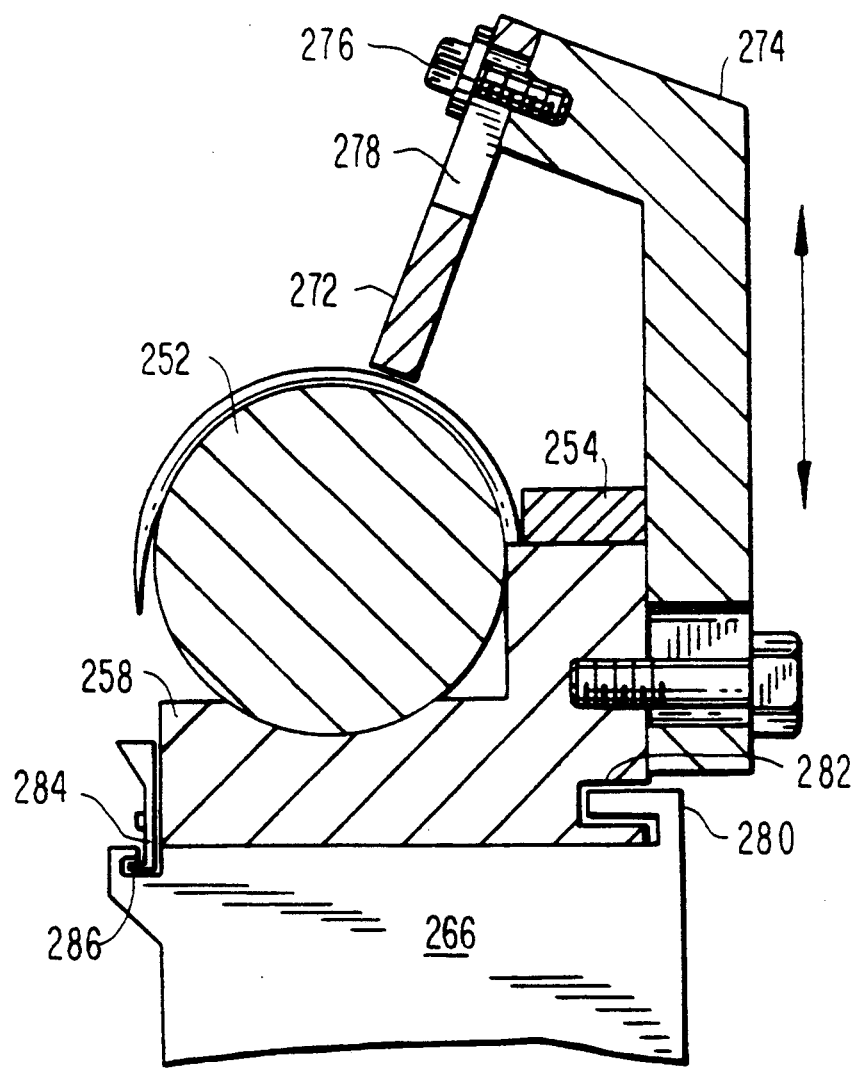
FIG. 30 is a cross-sectional view similar to FIG. 29, illustrating a rail of the feeding system removably secured to a vibrating frame.

In an alternative embodiment shown in FIG. 30, rail 252 may be removably secured to rail vibrating transformer 266 so that rail 252 may be utilized for storing needles and/or transporting needles between assembly stations. In this embodiment, vibrating transformer 266 includes interlocking flange 280 which is positioned into engagement with interlocking channel 282 of rail holder 258. Locking lever 284 which is rotatably secured to rail 252, is rotated into a locking engagement with locking channel 286 in vibrating transformer 266, thus locking rail 252 to transformer 266. To remove the rail from the transformer, an operator simply rotates locking lever 284 out of engagement with locking channel 286 and disengages interlocking channel 282 from interlocking flange 280.

Referring again to FIG. 28 and as noted above, the needles are traversed along the rail 252 to the position for presentation to pick and place system 216. Each needle is then sequentially picked from rail 252 via pick and place system 216. As shown, spacer bar 288 is secured to the end of rail 252 and is provided to prevent the needles from falling off the rail and to facilitate gripping of the needle by jaws 290 of pick and place system 216. Preferably, the upper portion 292 of spacer bar 288 is beveled so as to enable the jaws of the pick and place system to grab the curved portion 234a of needle 234.

Figure 31:
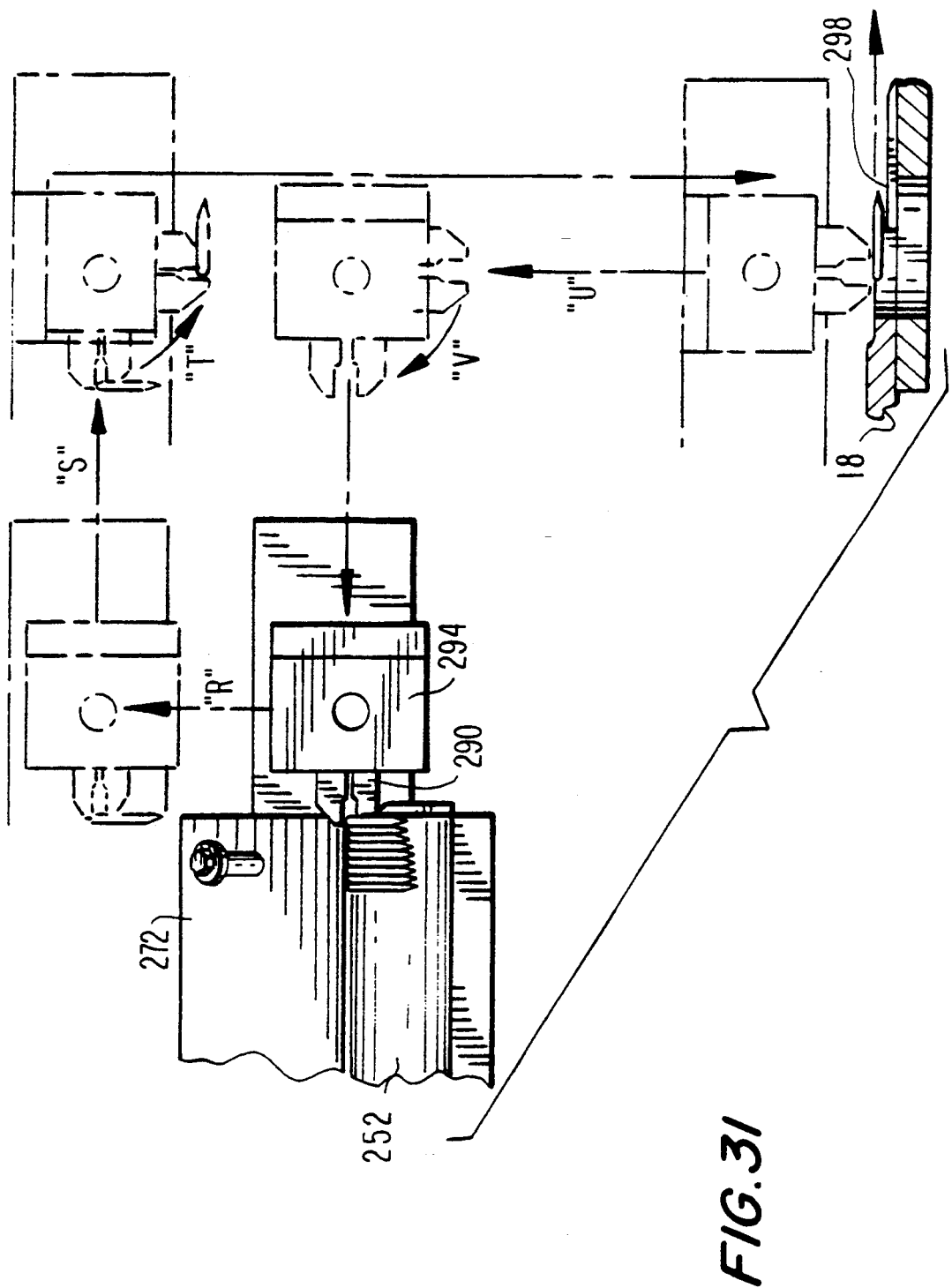
FIG. 31 is a front plan view of a portion of the pick and place system of the present invention illustrating the motion of the jaws when picking and placing a needle.

The pick and place system of the present invention will now be described with reference to FIGS. 27 and 31. As shown, pick and place system 216 includes jaws 290 movably secured to head 294, which are manipulated to grab needle 234 and thereafter place the needle onto needle pusher system 218 for subsequent processing. The drive mechanism for pick and place system 216 utilizes pneumatic pistons which respond to signals from control system 220 and facilitate vertical, horizontal and rotational movement of head 294, as well as, the opening and closing movement of jaws 290. Such pneumatic systems are known to those skilled in the art. In addition, other known sources may be utilized to move the head and jaws, for example, servo motors which are operatively connected to control system 220.

Figure 32:
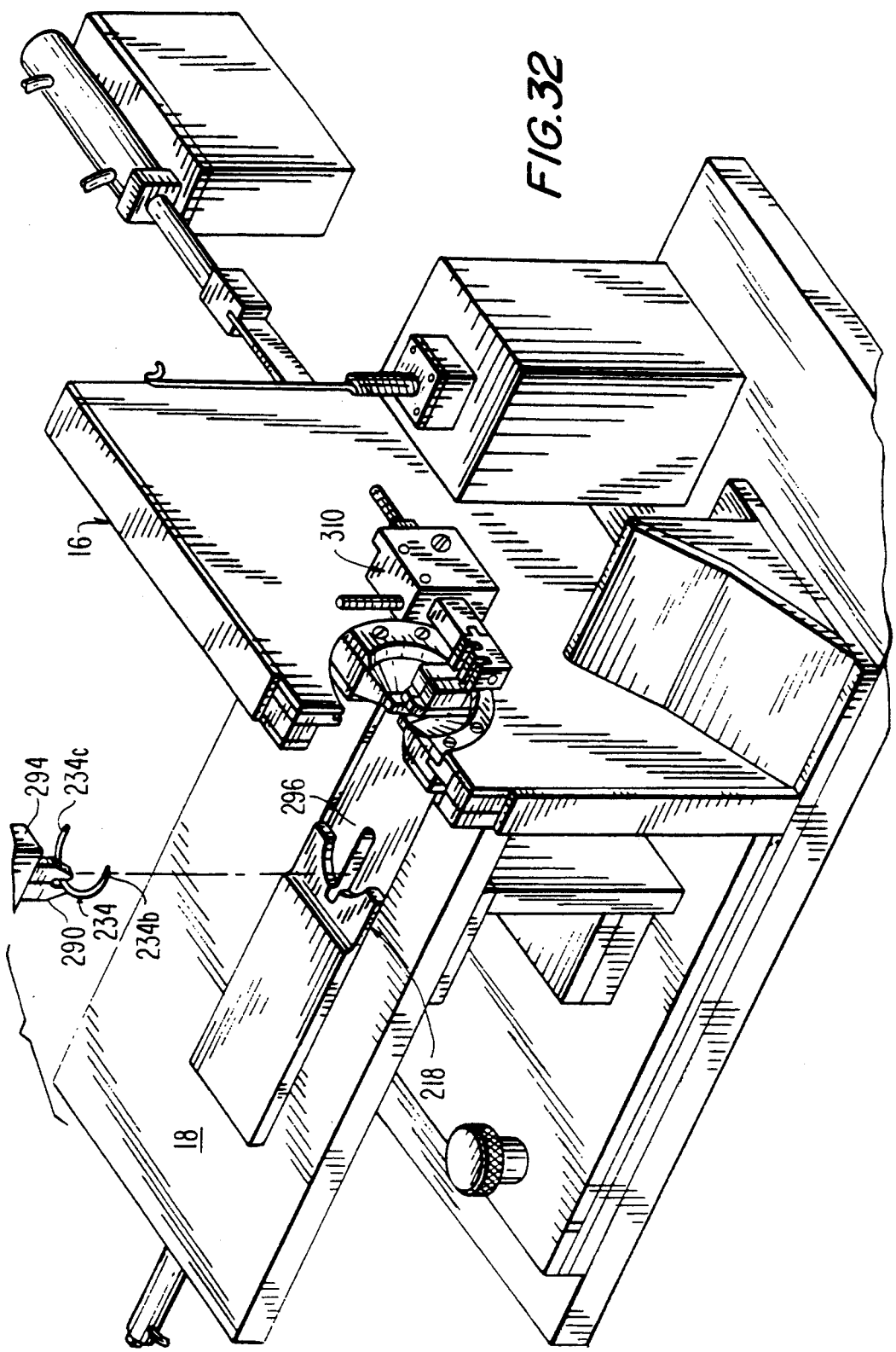
FIG. 32 is a perspective view of the needle pusher system of the present invention and the die rotating and crimping system, illustrating a manually operated suture guide attached to the die rotating and crimping system.

An illustration of the operational movement of jaws 290 and head 294 when it grabs a needle and deposits the needle onto needle pusher system 218 will be described with reference to FIGS. 31 and 32. Initially, jaws 290 of pick and place system 216 close to grab the first needle 234 at the end of rail 252. At this point, head 294 is then moved in a vertical direction, shown by arrow "R", away from rail 252 and then along a horizontal direction, shown by arrow "S", to a position in aligned communication with track 296 of needle pusher system 218. Thereafter, head 294 is rotated approximately 90°, shown by arrow "T", to cause the needle to align in a substantial parallel orientation to base plate 18 of needle pusher system 218, as shown. Head 294 is then lowered to a point adjacent base plate 18 and jaws 290 are opened to deposit the needle onto track 296 so that the needle point portion 234b and the barrel end portion 234c of the needle, face die rotating and crimping system 16, as shown in FIG. 32. Once the needle is released from jaws 290, head 294 is then retracted in a vertical direction, shown by arrow "U", and head 294 is rotated approximately 90°, shown by arrow "V", so that jaws 290 are in a position to grab the next needle presented on rail 252.

Figure 33:
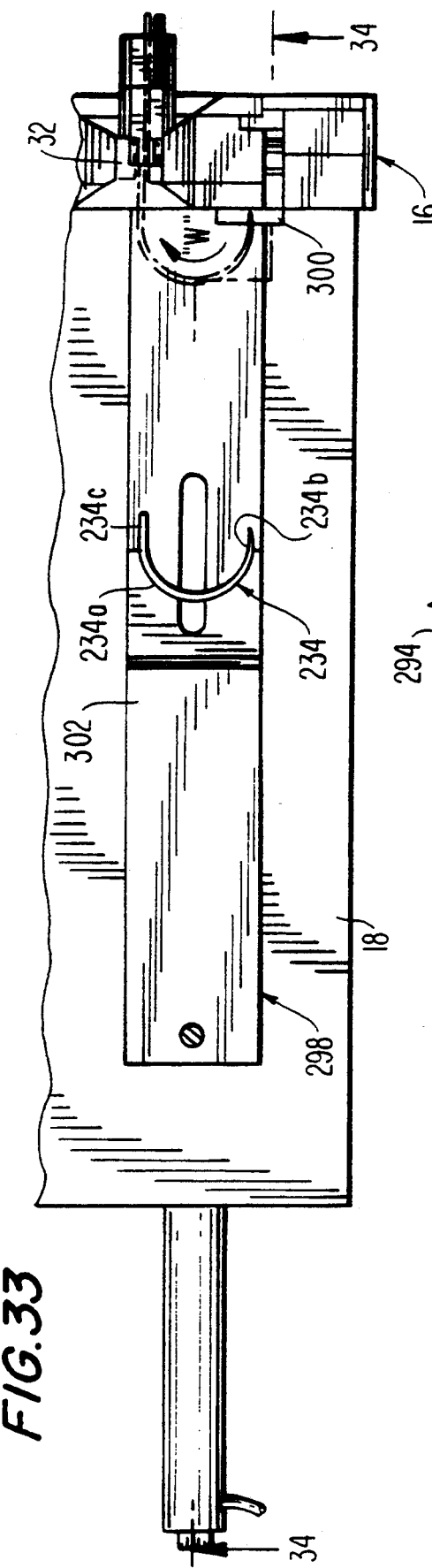
FIG. 33 is a top plan view of a portion of the needle pusher system of FIG. 32.
Figure 34:
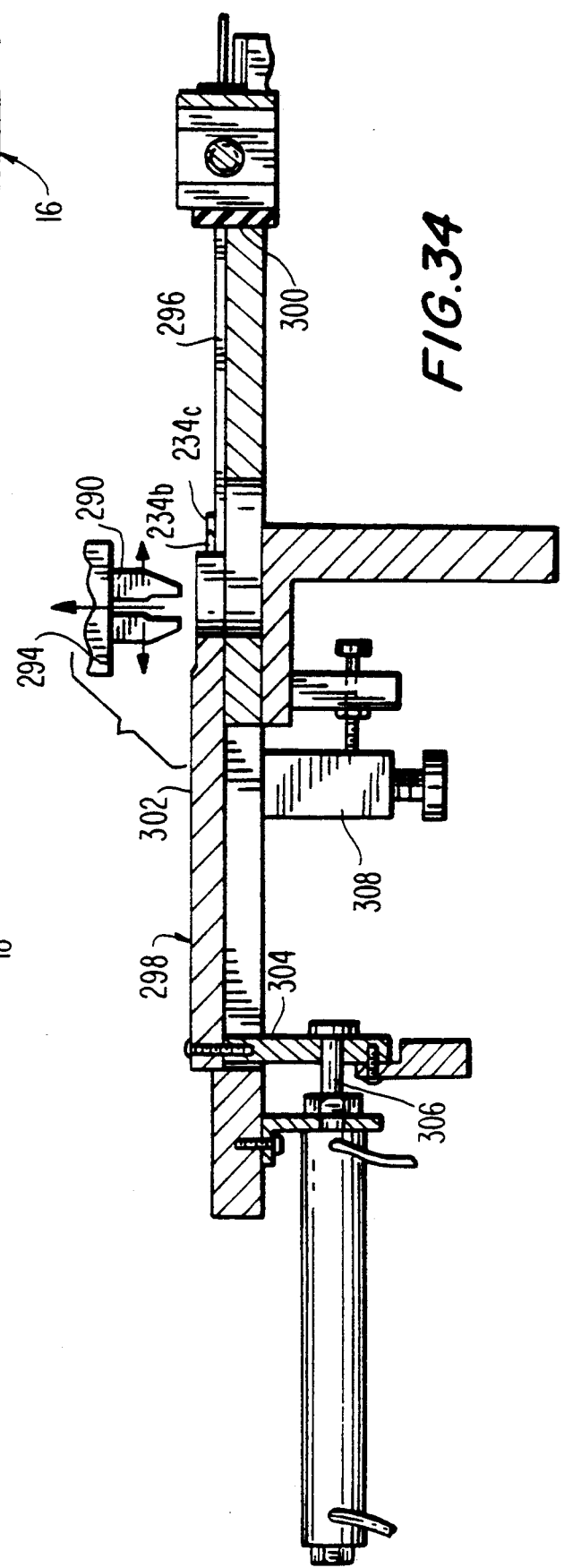
FIG. 34 is a side elevational view in partial cross-section of the needle pusher system of FIG. 33 taken along line 34—34 and illustrating the pneumatic piston for moving a slide member and a motion limiting switch.

At the same time or shortly after the needle is deposited onto needle pusher system 218, pusher unit 298 is activated by control system 220 to cause the needle to slide within track 296 toward the above described die rotating and crimping system. As shown in FIGS. 32-34, when the needle is deposited onto needle pusher assembly 218, curved portion 234a of needle 234 is facing the rear of pusher assembly 298. Thus when the needle is moved within track 296, the barrel end portion 234c of the needle is aligned with the needle gripper which maintains the needle in a fixed position to facilitate placement of the suture into the drilled end of the needle barrel portion.

When sliding the needle along track 296 the weight of the barrel portion of the needle has a tendency to cause barrel end portion 234c to lag behind the pointed end portion 234b of the needle. Delrin spring 300 is utilized to compensate for the lag by engaging pointed end portion 234c prior to the completion of the movement of pusher unit 298, thus causing barrel end portion 234c to rotate, shown by arrow "W" (FIG. 33), into position between dies 32 of die rotating and crimping system 16. The resilient features of spring 300 allow final positioning of the needle for swaging without damaging the pointed end portion of the needle, as shown in FIG. 33.

Continuing to refer to FIGS. 33 and 34, the preferred pusher unit 298 includes pusher arm 302, drive arm 304, piston 306 and limit switch 308. Preferably, piston 306 is a pneumatic piston which is responsive to control signals received from control system 220. Thus, after jaws 290 of pick and place system 216 deposit the needle onto track 296, a predetermined period of time may be allowed to lapse prior to activation of piston 306. Activation of piston 306 causes pusher arm 302 to move needle 234 toward die rotating and crimping system 16. Limit switch 308 is secured to base plate 18 and is provided to limit the movement of pusher arm 302 so as to position the barrel end portion of the needle between dies 32 of die rotating and crimping system 16 for subsequent crimping or swaging. Once the needle is positioned between dies 32, i.e., limit switch 308 is activated, pusher arm 302 is retracted, in response to retraction of piston 306, to receive the next needle deposited from the pick and place system.

Figure 35A:
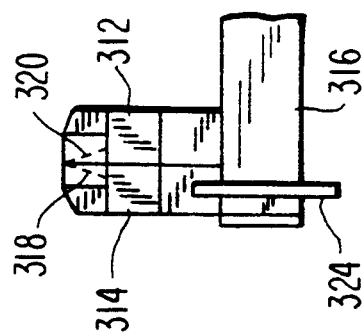
FIG. 35A is a top plan view of a portion of the manually operated needle suture guide of FIG. 35.
Figure 35:
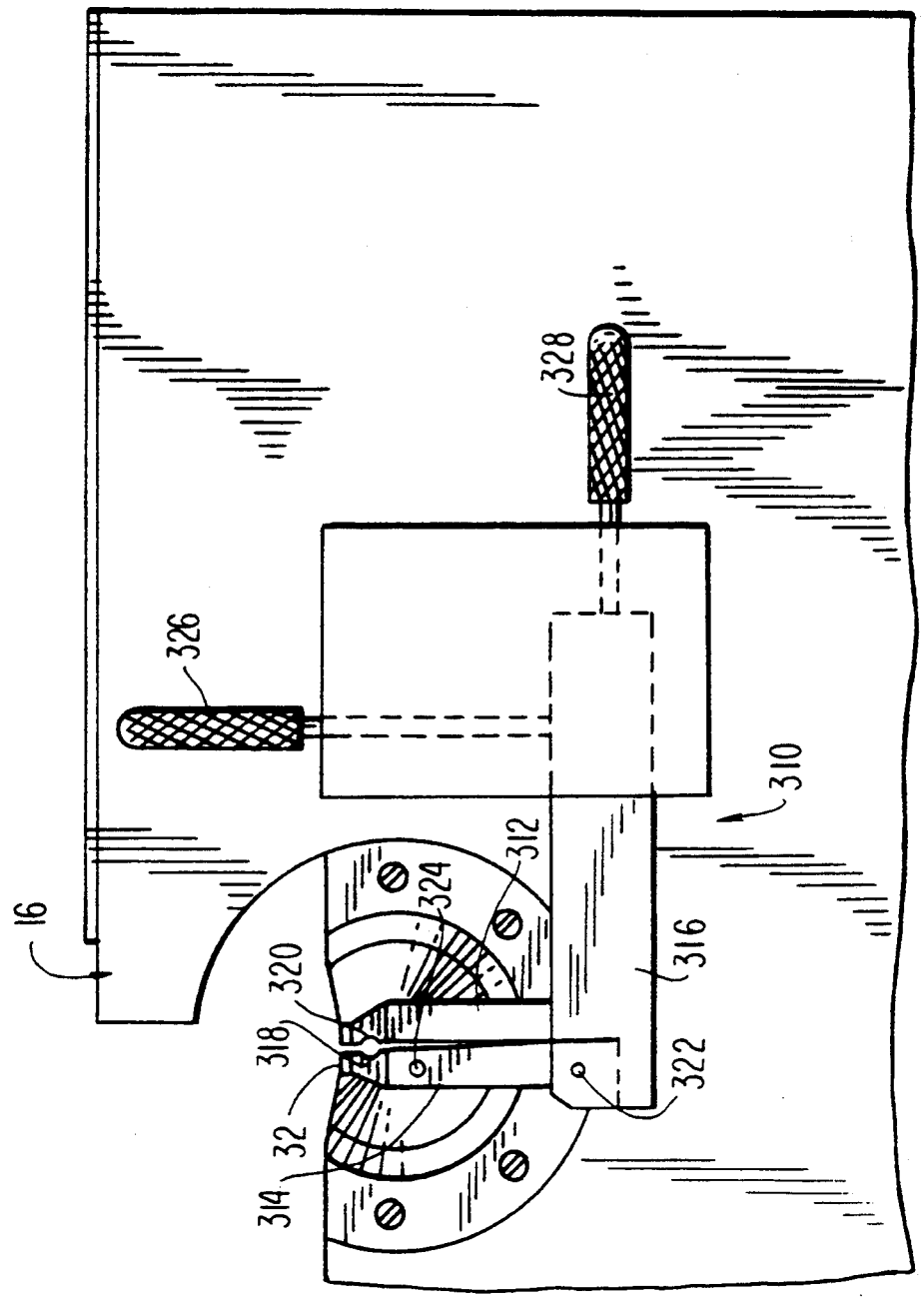
FIG. 35 is a side elevational view of a manually operated needle suture guide.
Figure 36:
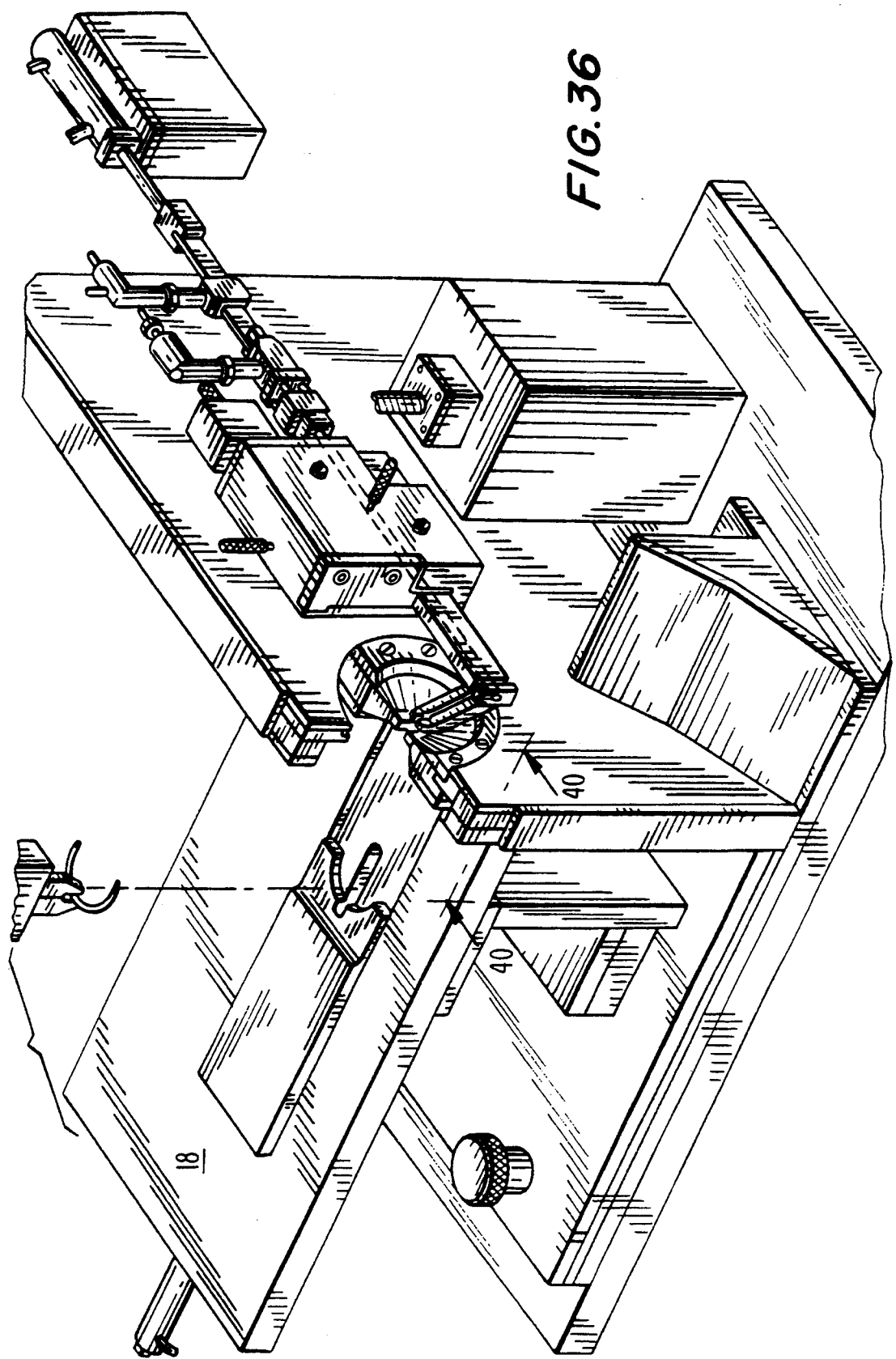
FIG. 36 is a perspective view similar to FIG. 32, illustrating an automatically operated needle holder and suture guide.

The present invention also provides manual and automatic suture guide assemblies which may be used to replace guide member 30 described above and shown in FIG. 4. Manual suture guide assembly 310, shown in FIGS. 32 and 35, is secured to die rotating and crimping system 16 and is provided to guide the insertion of a suture into the bore in the barrel end portion of the needle. The suture guide assembly 310 also limits the movement of the needle as it is positioned between dies 32. As shown, suture guide assembly 310 includes stationary guide arm 312 and pivoting guide arm 314 both of which are secured to support member 316. Each guide arm includes semi-circular portions 318 and 320, respectively, which form the opening to guide the suture into the bore in the needle when the guide arms are in the closed position. Preferably, as shown in FIG. 35A, portions 318 and 320 are tapered to allow a wide insertion portion where an operator can insert the suture and which narrows to the approximate diameter of the bore in the needle to guide the suture into the bore. Pivoting guide arm 314 is pivotally secured to support member 316 via pivot pin 322 and lever arm 324 is provided to allow the operator to pivot guide arm 314 and remove the swaged surgical suture. Preferably, as shown in FIG. 35, suture guide assembly 310 includes thumb screws 326 and 328 which allow vertical and horizontal adjustment of the guide arms for proper alignment with dies 32 and the needle bore.

The automatic suture guide assembly of the present invention is shown in FIGS. 36-40. Automatic suture guide assembly 330 is secured to die rotating and crimping system 16 and is provided to limit the movement of the needle as it is positioned between dies 32, to guide the insertion of a suture into the drilled end of the needle, i.e., the needle bore, prior to swaging, and to automatically open the guide arms to allow removal of the swaged surgical suture. Automatic suture guide assembly 330 includes stationary guide arm 332 which is secured to support member 334 and movable guide arm 336. Each guide arm includes tapered semi-circular portions 338 and 340 which are similar to the above described semi-circular portions 318 and 320 and which guide the suture into the bore in the end face of the barrel end portion of the needle.

Movable guide arm 336 is secured to piston arm 342 which moves the guide arm between an open position, shown in FIG. 37 and a closed position, shown in FIG. 38, in response to control signals from control system 220. Piston arm 342 is slidably positioned through adjusting frame 344 into drive cylinder assembly 346. Preferably, drive cylinder assembly 346 is a pneumatic cylinder responsive to control signals received from control system 220.

Figure 39:
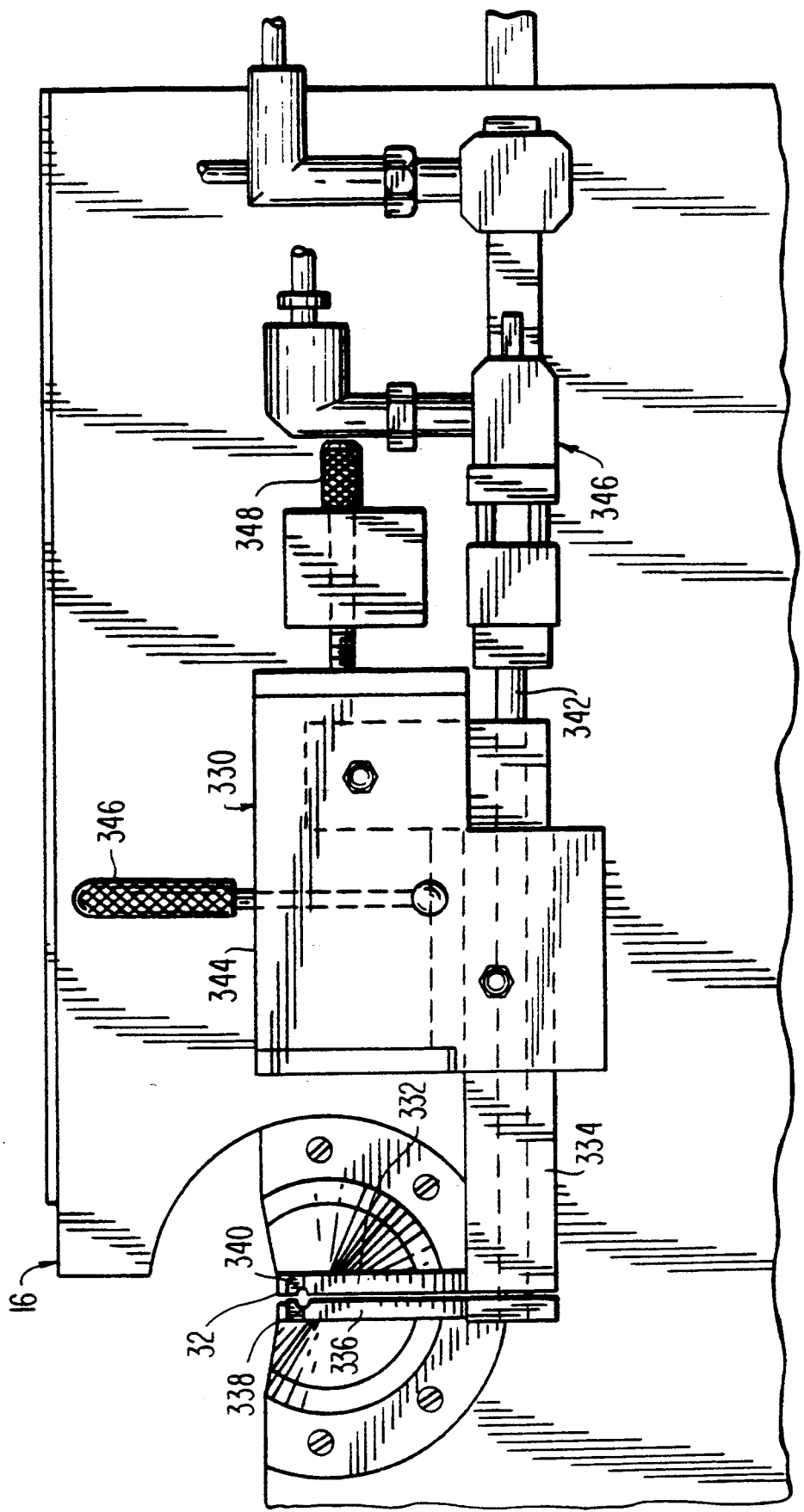
FIG. 39 is a side elevational view of a portion of the automatically operated needle suture guide of FIG. 36, illustrating two of the three dimensional adjusting screws.

Referring to FIGS. 39 and 40, adjusting frame 344 includes thumb screws 346, 348 and 350 which facilitate adjustment of the guide arms 332 and 336 so that the guide arms properly align with dies 32 of die rotating and crimping system 16 and the needle bore.

Once the needles are gripped by needle gripper 22, shown in FIGS. 2-4 and described above, a predetermined period of time may be allowed to lapse before control system 220 activates the above described die rotating and crimping system 16 which operates in a manner described above.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. Apparatus for feeding surgical needles to a suture crimping apparatus, which comprises:
   a container for receiving curved surgical needles and orientating the surgical needles in a predefined position for subsequent processing;
   a transmission member for receiving the orientated needles from said container at a receiving position and transferring the needles to a presenting position;

means for transferring the needles between said presenting position and a crimping position, said transferring means including:

means for grasping needles in said presenting position and for transferring said grasped needle to a needle pusher track; and means for moving the needle along said pusher track to said crimping position.

2. The apparatus according to claim 1, wherein said container comprises a vibratory bowl having at least one sweep positioned on a bottom portion of said bowl and at least one ramp which transfers the needles from said bottom portion of the bowl to said receiving position, said receiving position being located at a side wall portion of said bowl.

3. The apparatus according to claim 2, wherein said at least one sweep is configured and dimensioned to orient a curved portion of the needles against said side wall of said bowl.

4. The apparatus according to claim 2, wherein said at least one ramp comprises a single ramp secured to said side wall of said bowl so as to define a substantially spiral shape member which extends along said side wall from said bottom portion to said receiving position.

5. The apparatus according to claim 1, wherein said transmission member comprises a vibratory rail having a substantially cylindrical shape and which is adapted to support and transfer the needles to said presenting position.

6. The apparatus according to claim 1, wherein said grasping and transferring means comprises
a drive member adapted for movement between said presenting position and said crimping position; and
a pair of jaws secured to said drive member and movable between an open position and a closed position.

7. Apparatus for feeding surgical needles to a suture crimping apparatus, which comprises:
a container for receiving curved surgical needles and orientating the surgical needles in a predefined position for subsequent processing, said container including a vibratory bowl having at least one sweep positioned on a bottom portion of said bowl and at least one ramp which transfers the needles from said bottom portion of the bowl to a receiving position, said receiving position being located at a side wall portion of said bowl, said vibratory bowl being coated with polyurethane;
a transmission member for receiving the orientated needles from said container at said receiving position and transferring the needles to a presenting position; and
means for transferring the needles between said presenting position and a crimping position.

8. Apparatus for feeding surgical needles to a suture crimping apparatus, which comprises:
a container for receiving curved surgical needles and orientating the surgical needles in a predefined position for subsequent processing;
a transmission member for receiving the orientated needles from said container at a receiving position and transferring the needles to a presenting position, said transmission member including a vibratory rail having a substantially cylindrical shape and which is adapted to support and transfer the needles to said present position, said rail having a radius equal to or less than the radius of curvature of the curved surgical needle; and means for transferring the needles between said presenting position and a crimping position.

9. Apparatus for receiving and orienting curved surgical needles, which comprises a container having a base, at least one side wall and a needle receiving member positioned on said base, said container having at least one sweep positioned on said base for orienting curved surgical needles to a predetermined orientation and at least one ramp for processing the curved surgical needles from said base to a needle presenting position on said side wall, said container being coated with a polymer whereby damage to points of the needles is substantially avoided.

10. The apparatus according to claim 9 further comprising means for vibrating said container at a predetermined rate.

11. The apparatus according to claim 10, wherein said vibrating means comprises a frame adapted to support said container and a transformer for vibrating said frame.

12. The apparatus according to claim 9, wherein said container comprises a stainless-steel bowl.

13. Apparatus for feeding surgical needles to a suture crimping apparatus while minimizing needle point damage, which comprises:
a container for receiving curved surgical needles and orientating the surgical needles in a predefined position for subsequent processing whereby damage to needle points is substantially avoided;
a transmission member for receiving the orientated needles from said container at a receiving position and transferring the needles to a presenting position whereby damage to said needle points is substantially avoided;
a drive member adapted for movement between said presenting position and a crimping position;
a pair of jaws secured to said drive member and movable between an open position and a closed position to grasp and transfer a needle to a needle pusher track; and
a pusher unit to move the needles along said needle pusher track whereby damage to said needle points is substantially avoided.

14. Apparatus for feeding surgical needles to a needle crimping apparatus while minimizing needle point damage, which comprises:
a container configured to receive curved surgical needles, said container having a sweep member disposed within said container and configured to orient the surgical needles in a predefined position for subsequent processing;
a transmission member operatively associated with said container, said transmission member receiving the orientated needles from said container at a receiving position and transferring the needles to a presenting position;
a drive member mounted for movement between said presenting position and a crimping position;
a pair of jaws secured to said drive member and movable between an open position and a closed position to grasp and transfer a needle from said presenting position to a needle pusher track; and
a pusher unit operatively associated with said needle pusher track to move the needles along said needle pusher track to said crimping position, whereby damage to said needle points is substantially avoided as said needles are moved to said crimping position.

* * * * *